(12) United States Patent
Johnson et al.

(10) Patent No.: US 7,405,289 B2
(45) Date of Patent: Jul. 29, 2008

(54) PANCREATIC ISLET TRANSCRIPTION FACTOR AND USES THEREOF

(75) Inventors: Jeffrey D. Johnson, Moraga, CA (US); John F. Palma, San Ramon, CA (US); Anthony C. Schweitzer, Menlo Park, CA (US); John E. Blume, Danville, CA (US)

(73) Assignee: Metabolex, Inc., Hayward, CA (US)

( * ) Notice: Subject to any disclaimer, the term of this patent is extended or adjusted under 35 U.S.C. 154(b) by 358 days.

(21) Appl. No.: 10/533,593

(22) PCT Filed: Nov. 13, 2003

(86) PCT No.: PCT/US03/36131

§ 371 (c)(1), (2), (4) Date: May 2, 2005

(87) PCT Pub. No.: WO2004/044170

PCT Pub. Date: May 27, 2004

(65) Prior Publication Data

US 2006/0264611 A1    Nov. 23, 2006

Related U.S. Application Data

(60) Provisional application No. 60/425,968, filed on Nov. 13, 2002.

(51) Int. Cl.
*C12Q 1/68* (2006.01)
*C07H 21/04* (2006.01)

(52) U.S. Cl. .......................... 536/23.5; 435/6; 530/350

(58) Field of Classification Search ....................... None
See application file for complete search history.

(56) References Cited

FOREIGN PATENT DOCUMENTS

WO   WO01/75067   * 10/2001

OTHER PUBLICATIONS

Carnici et al. (Methods Enzymol., 1999, vol. 303, p. 19-44).*
Collins et al. (PNAS, 2002, vol. 99, No. 26, p. 16899-16903).*
Sequence alignments.*

* cited by examiner

*Primary Examiner*—Gary Benzion
*Assistant Examiner*—Stephanie K Mummert
(74) *Attorney, Agent, or Firm*—Townsend and Townsend and Crew LLP

(57) ABSTRACT

The present invention provides a pancreatic islet transcription factor and methods of treating and diagnosing diabetes.

16 Claims, 8 Drawing Sheets

Figure 5

|  | | | | 10 | | | *20 | | | 30 |
|---|---|---|---|---|---|---|---|---|---|---|
| ICRFX | | TLQWL | EENY | LVCEGY | CLPRC | IEYA | HYLD | FC |
| RFX4 | | TLQWL | EENY | IAEGY | CTPRS | ALYM | HYLD | FG |
| RFX5 | AYRWI | RNHLE | HTDTC | LPKQS | VYDA | RKYC |
| daf-19 | TVNWL | FENGE | IGEG- | SGPRC | ELYN | DHYK | KC |
| RFX3 | HLEQWL | LDNYE | TAEGVSL | PRST | IRSS | HYZL | RHC |
| RFX2 | HLEQWL | LDNYE | AEGVSL | PRST | IRSS | HYVL | RHC |
| RFX1 | TVQWL | LDNYE | ARGVSL | PRST | ICHY | ELHC |

TLQWL . NYE AEGVSLPRS . LY . HYL . HC

|  | | | | 40 | | | *50 | | | *60 |
|---|---|---|---|---|---|---|---|---|---|---|
| ICRFX | RK- | EKLE | ACAAT | FGKT | RQKP | LET | RRL |
| RFX4 | EK- | NDTQ | PVNAAS | FGKI | RQQP | QET | RRL |
| RFX5 | ESL | ACCR | PLSTAN | FGKI | DPRE | DIKA | RRL |
| daf-19 | AE- | HRMD | PVNAAS | FGKL | IRSV | HNEK | TRL |
| RFX3 | QE- | HKLE | DPVNAAS | FGKL | IRSI | MGIR | TRRL |
| RFX2 | QE- | HKLE | DPVNAAS | FGKL | IRSV | MGIR | TRRL |
| RFX1 | QE- | QKLE | PVNAAS | EGKL | IRSV | MGLR | TRRL |

E . KL . PVNAASFGKLIRS . F . L . TRRL

|  | | | *70 | | | 80 | | | 90 |
|---|---|---|---|---|---|---|---|---|---|
| ICRFX | *GTRGH | SKYHY | VGI GIKE |
| RFX4 | GTRGQ | SKYHY | VGTAVRE |
| RFX5 | GGRGQ | SRYCY | SGLRRKT |
| daf-19 | GTRGN | SKYHY | VGIRRLKD |
| RFX3 | GTRGN | SKYHY | VGJERVKP |
| RFX2 | CNRGN | SKAHY | VGJRLKP |
| RFX1 | CTRGN | SKYHY | VGLRIKA |

GTRGNSKYHYYGIR.K

Figure 6

```
                    10              20              30
ICRFX    K V D T I M M Y K T H C Q C I D N A L N G N E E E I Q H
daf19    E L N S E I D I V E I C R E E I A L I K N I D A S V E D
RFX1     D I K A F Q V L R H C E A L V D V M V N L Q F T L V E T
RFX2     D V K A E Q L V Y R H C E A T V D V V M N L Q R H Y I E K
RFX4     K V S T F I M M Y R T H C Q R I L D T V I R A N F D E V Q S
RFX3     D I K S L Q S L R E H C E A L T D V V V N L Q E S L I E K
         .   . L       Y R   H C     I L D       N . . F . . E 40              50              60
ICRFX    F L L H F W
daf19    T I W S K F W
RFX1     L W L K T F W
RFX2     L W L S L F W
RFX4     F L L H F W
RFX3     L W Q T F W
         W           F W
```

Figure 7

```
                        10                  20              30
ICRFX   L K V L T D V L P - A T M Q E M P E S L A D T R N F A
RFX4    L K K A I S G V M P - T V I Q A L D D S L T Q V R K F A
RFX1    L V Q G L V E L P - D V I R P I P S A L T Q A T R N F A
daf19   I Y Q T I V D T E P N V L S E L S T G M Q T C R T F A L Y . . L Y . . L I P . . . L . . P . . L T Q . I R . F A
                                                            60

40                  50
ICRFX   K N W E Q W V S S E K V A L T H A M V R K S L L
RFX4    Q L D E W L K V A L S W T H A M V R K S L L
RFX1    K S L E S W L E T H A M Y L K S L
daf19   K N I D V Y L

PANCREATIC ISLET TRANSCRIPTION FACTOR AND USES THEREOF

CROSS-REFERENCE TO RELATED PATENT APPLICATIONS

The present application claims benefit of priority to U.S. Provisional Patent Application No. 60/425,968, filed Nov. 13, 2002, which is incorporated by reference in its entirety for all purposes.

BACKGROUND OF THE INVENTION

Insulin, a hormone required for metabolic homeostasis, is produced only in the pancreatic beta cell. Type I Diabetes is characterized by a rapid loss of beta cell mass and a sharp decrease in pancreatic insulin content. A decline in beta cell mass and function is also characteristic of Type II Diabetes. Intervention to improve beta cell mass and function is a major goal of diabetes therapeutics.

Perturbations in the expression or function of numerous islet transcription factors have been demonstrated to cause beta cell dysfunction. In humans, mutations in islet transcription factors HNF4alpha, HNF4beta, HNF1alpha, and pdx-1 lead to Maturity Onset Diabetes of the Young (MODY) syndromes via the resulting deficit in beta cell function. See, e.g., Froguel, P & Velho, G, *Trends Endocrinol Metab* 10: 142-146 (1999)). Functional deletion of other islet transcription factors (e.g. nkx6.1, nkx2.2, isl-1, neuroD/beta2, PAX6) in mice also lead to beta cell and insulin deficits and diabetes. See, e.g., Melloul, D. et al., *Diabetes* 45: 309-326 (2002); Sander M et al., *Genes Dev* 11: 1662-1673 (1997); Sander M et al., *Development* 127: 5533-5540 (2000). Overexpression of pdx1 in islets can lead to restoration of beta cell mass and function in the context of diabetogenic mutations in other proteins (Kushner J A et al., *J Clin Invest* 109: 1193-1201 (2002)). Overexpression of pdx-1 and isl-1 in enteric stem cell populations confers on them the ability to produce insulin (Kojima H et al., *Diabetes* 51: 1398-1408 (2002)). It is clear that the proper complement of islet transcription factors is crucial for maintenance of a stable metabolic state, and that, in some cases, it is possible to confer on certain cells the ability to express insulin by providing for increased expression of islet transcription factors.

There are five known RFX genes in humans. RFX1, RFX2, RFX3 and RFX4 share conserved DNA-binding domains, dimerization domains, and domains of undefined function called B and C. The dimerization domains allow RFX1-4 proteins to homo- and heterodimerize. This dimerization function is involved in the transcriptional function of these proteins. RFX 1, 2 and 3 also have an additional conserved A domain. RFX5 has the conserved DBD, but lacks the dimerization and A, B, and C domains. RFX5 controls transcription from the MHC class II gene promoter, and mutations in RFX5 lead to the bare lymphocyte syndrome, a serious immunodeficiency disorder (Reith W and Mach B, *Annu. Rev. Immunol.* 19: 331-373 (2001)).

The molecular mechanisms that control a cell's ability to produce insulin remains poorly understood. The present invention addresses this and other problems.

BRIEF SUMMARY OF THE INVENTION

The present invention provides an isolated nucleic acid encoding an IC-RFX polypeptide at least 70% identical to SEQ ID NO:2. In some embodiments, the nucleic acid encodes SEQ ID NO:2. In some embodiments, the nucleic acid comprises SEQ ID NO:1.

The present invention also provides an isolated nucleic acid encoding a polypeptide comprising in the following order: a proline/glutamine rich domain, an RFX DNA binding domain (SEQ ID NO:4), an RFX B domain (SEQ ID NO:5), an RFX C domain (SEQ ID NO:6), a dimerization domain (SEQ ID NO:7) and a serine/threonine domain.

The present invention also provides an expression cassette comprising a promoter operably linked to the nucleic acid encoding an IC-RFX polypeptide at least 70% identical to SEQ ID NO:2.

The present invention also provides an isolated nucleic acid that specifically hybridizes following at least one wash in 0.2×SSC at 55° C. for 20 minutes to a probe comprising SEQ ID NO:1.

The present invention also provides an isolated IC-RFX polypeptide comprising an amino acid sequence at least 70% identical to SEQ ID NO:2. In some embodiments, the polypeptide comprises SEQ ID NO:2. In some embodiments, the polypeptide specifically binds to antibodies generated against SEQ ID NO:2.

The present invention also provides an antibody that specifically binds to SEQ ID NO:2.

The present invention also provides a host cell transfected with the nucleic acid encoding an IC-RFX polypeptide at least 70% identical to SEQ ID NO:2. In some embodiments, the cell is a pancreatic islet cell. In some embodiments, the cell is an islet β-cell.

The present invention also provides methods of diagnosing a subject with diabetes or a susceptibility for diabetes. In some embodiments, the methods comprise detecting in a sample from the subject a polynucleotide that hybridizes to a probe comprising SEQ ID NO:1 following at least one wash in 0.2×SSC at 55° C. for 20 minutes. In some embodiments, the polynucleotide is detected by hybridization. In some embodiments, the polynucleotide is detected by amplification of the polynucleotide. In some embodiments, the nucleotide sequence of the polynucleotide is determined.

In some embodiments, the method comprises detecting the level of an IC-RFX polypeptide or transcript encoding the IC-RFX polypeptide in a sample from the subject, wherein a modulated level of the polypeptide or transcript in the sample compared to a level of the polypeptide or transcript in a non-diabetic individual indicates that the subject is diabetic or is predisposed for at least some pathological aspects of diabetes, and wherein the IC-RFX polypeptide is at least 70% identical to SEQ ID NO:2. In some embodiments, the polypeptide comprises SEQ ID NO:2. In some embodiments, the polypeptide is detected by an antibody.

The invention also provides methods for identifying an agent for treating a diabetic or pre-diabetic individual. In some embodiments, the method comprises the steps of (i) contacting an agent to a mixture comprising an IC-RFX polypeptide at least 70% identical to SEQ ID NO:2; and (ii) selecting an agent that modulates the expression or activity of the polypeptide or that binds to the polypeptide. In some embodiments, the method further comprising selecting an agent that modulates insulin expression of a cell. In some embodiments, step (ii) comprises selecting an agent that modulates expression of the polypeptide. In some embodiments, step (ii) comprises selecting an agent that modulates the activity of the polypeptide. In some embodiments, step (ii) comprises selecting an agent that specifically binds to the polypeptide. In some embodiments, the polypeptide is expressed in a cell and the cell is contacted with the agent. In some embodiments, the polypeptide is SEQ ID NO:2.

The present invention also provides methods of treating a diabetic or pre-diabetic animal. In some embodiments, the methods comprise administering to the animal a therapeutically effective amount of an agent identified by (i) contacting an agent to a mixture comprising an IC-RFX polypeptide at least 70% identical to SEQ ID NO:2; and (ii) selecting an agent that modulates the expression or activity of the polypeptide or that binds to the polypeptide. In some embodiments, the agent is an antibody. In some embodiments, the antibody is a monoclonal antibody. In some embodiments, the animal is a human.

The present invention also provides methods of introducing an expression cassette into a cell. In some embodiments, the methods comprise introducing into the cell an expression cassette comprising a promoter operably linked to a polynucleotide encoding an IC-RFX polypeptide at least 70% identical to SEQ ID NO:2. In some embodiments, the polypeptide comprises SEQ ID NO:2. In some embodiments, the polynucleotide comprises SEQ ID NO:1. In some embodiments, the method further comprising introducing the cell into a human. In some embodiments, the human is diabetic. In some embodiments, the human is prediabetic. In some embodiments, the cell is from the human. In some embodiments, the cell is a pancreatic islet cell. In some embodiments, the cell is an islet β-cell.

The present invention also provides for dimers comprising at least one IC-RFX polypeptide. In some embodiments, the dimer is a homodimer of IC-RFD polypeptides. In some embodiments, the dimer is a heterodimer comprising one IC-RFX polypeptide and a second polypeptide. In these embodiments, the second polypeptide is selected from an RFX transcription factor, e.g., RFX1, RFX2, RFX3, RFX4 or RFX5.

DEFINITIONS

An "IC-RFX transcription factor" or IIC-RFX polypeptide" refers to a polypeptide that is a member of the RFX transcription factor family and has a structure as illustrated in FIG. 4. IC-RFX polypeptides comprise domains in the following order: a proline/glutamine rich domain, an RFX DNA binding domain, an RFX B domain, an RFX C domain, a dimerization domain and a serine/threonine domain. An exemplary consensus sequence for IC-RFX polypeptides is SEQ ID NO:3. Exemplary IC-RFX polypeptides are substantially identical to SEQ ID NO:2.

A "proline/glutamine" domain as used herein refers to an amino acid subsequence between about 40 to about 150 amino acids, and often between 60-90 amino acids, that comprise at least about 8% or at least about 10% proline or glutamine residues, i.e., the sum of proline and glutamine residues make up at least 8 or 10% of the amino acids in the domain.

An "RFX DNA binding domain" as used herein, refers to an amino acid subsequence of between about 50 and about 100 amino acids that has a sequence substantially identical to SEQ ID NO:4 or conservative substitutions thereof. Exemplary RFX DNA binding domains include, e.g.,

TLQWLEENYIVCEGVCLPRCILYAHYLDFCRKEKLEPACAATFGKTIRQK
FPLLTTRRLGTRGHSKYHYYGIGIKE.

An "RFX B domain," as used herein, refers to an amino acid subsequence of between about 20 and about 60 amino acids that has a sequence substantially identical to SEQ ID NO:5 or conservative substitutions thereof. Exemplary RFX DNA binding domains include, e.g., KVDTLIMMYKTHC-QCILDNAINGNFEEIQHFLLHFW.

A "RFX C domain," as used herein, refers to an amino acid subsequence of between about 20 and about 60 amino acids that has a sequence substantially identical to SEQ ID NO:6 or conservative substitutions thereof. Exemplary RFX DNA binding domains include, e.g.,

LYKVLTDVLIPATMQEMPESLLADIRNFAKNWEQWVVSSL.

A "dimerization domain," as used herein, refers to an amino acid subsequence of between about 150 and about 200 amino acids that has a sequence substantially identical to SEQ ID NO:7 or conservative substitutions thereof. Exemplary RFX DNA binding domains include, e.g., RFVSSLKRQTSFLHLAQIARPALFDQHVVNSMVSDIERVDLNSIGSQALL
TISGSTDTESGIYTEHDSITVFQELKDLLKKNATVEAFIEWLDTVVEQRV
IKTSKQNGRSLKKRAQDFLLKWSFFGARVMHNLTLNNASSFGSFHLIRML
LDEYILLAMETQFNNDKEQELQNLLDKYM.

A "serine/threonine" domain as used herein refers to an amino acid subsequence between about 50 to about 200 amino acids, and often between 100-500 amino acids, that comprises at least about 15% and sometimes at least about 20% proline or glutamine residues.

An "IC-RFX nucleic acid" or an "IC-RFX polynucleotide" refers to a nucleic acid or polynucleotide encoding an IC-RFX polypeptide or fragment thereof. Exemplary IC-RFX polynucleotides include, e.g., SEQ ID NO:1.

A "beta cell phenotype" refers to the expression of markers that normally distinguish the beta cells from the other pancreatic islets cells. For example, beta cells express insulin in a glucose dependent manner, express Nkx6.1 or glucokinase.

A "lean individual," when used to compare with a sample from a patient, refers to an adult with a fasting blood glucose level less than 110 mg/dl or a 2 hour PG reading of 140 mg/dl. "Fasting" refers to no caloric intake for at least 8 hours. A "2 hour PG" refers to the level of blood glucose after challenging a patient to a glucose load containing the equivalent of 75 g anhydrous glucose dissolved in water. The overall test is generally referred to as an oral glucose tolerance test (OGTT). See, e.g., *Diabetes Care*, Supplement 2002, American Diabetes Association: Clinical Practice Recommendations 2002. The level of a polypeptide in a lean individual can be a reading from a single individual, but is typically a statistically relevant average from a group of lean individuals. The level of a polypeptide in a lean individual can be represented by a value, for example in a computer program.

A "pre-diabetic individual," when used to compare with a sample from a patient, refers to an adult with a fasting blood glucose level greater than 110 mg/dl but less than 126 mg/dl or a 2 hour PG reading of greater than 140 mg/dl but less than 200 mg/dl. A "diabetic individual," when used to compare with a sample from a patient, refers to an adult with a fasting blood glucose level greater than 126 mg/dl or a 2 hour PG reading of greater than 200 mg/dl.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or "percent similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Examples of an algorithm that is suitable for determining percent sequence identity and sequence similarity include the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance.

For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid that contains sequence information for a structural RNA such as rRNA, a tRNA, or the primary amino acid sequence of a specific protein or peptide, or a binding site for a transacting regulatory agent. This phrase specifically encompasses degenerate codons (i.e., different codons which encode a single amino acid) of the native sequence or sequences that may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that otherwise are expressed abnormally, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors," "activators," and "modulators" of IC-RFX expression or of IC-RFX activity are used to refer to inhibitory, activating, or modulating molecules, respectively, identified using in vitro and in vivo assays for IC-RFX expression or IC-RFX activity, e.g., ligands, agonists, antagonists, and their homologs and mimetics. The term "modulator" includes inhibitors and activators. Inhibitors are agents that, e.g., inhibit expression of IC-RFX or bind to, partially or totally block stimulation or enzymatic activity, decrease, prevent, delay activation, inactivate, desensitize, or down regulate the activity of IC-RFX, e.g., antagonists. Activators are agents that, e.g., induce or activate the expression of IC-RFX or bind to, stimulate, increase, open, activate, facilitate, enhance activation or enzymatic activity, sensitize or up regulate the activity of IC-RFX, e.g., agonists. Modulators include naturally occurring and synthetic ligands, antagonists, agonists, small chemical molecules and the like. Such assays for inhibitors and activators include, e.g., applying putative modulator compounds to pancreatic cells or other cells expressing IC-RFX, in the presence or absence of IC-RFX modulators and then determining the functional effects on IC-RFX activity, as described above. Samples or assays comprising IC-RFX that are treated with a potential activator, inhibitor, or modulator are compared to control samples without the inhibitor, activator, or modulator to examine the extent of effect. Control samples (untreated with modulators) are assigned a relative IC-RFX activity value of 100%. Inhibition of IC-RFX is achieved when the IC-RFX activity value relative to the control is about 80%, optionally 50% or 25-1%. Activation of IC-RFX is achieved when the IC-RFX activity value relative to the control is 110%, optionally 150%, optionally 200-500%, or 1000-3000% higher.

BRIEF DESCRIPTION OF THE DRAWINGS

FIG. 5 illustrates an amino acid sequence alignment of the DNA binding domains of IC-RFX and other mammalian RFX proteins and the *C. elegans* RFX protein daf-19. A consensus sequence is shown at the bottom of each alignment. Asterisks mark the residues involved in DNA binding in RFX1. Boxed and shaded residues define broadly conserved residues.

FIG. 6 illustrates an amino acid sequence alignment of the B domains of IC-RFX and other mammalian RFX proteins and the *C. elegans* RFX protein daf-19. A consensus sequence is shown at the bottom of each alignment. Boxed and shaded residues define broadly conserved residues.

FIG. 7 illustrates an amino acid sequence alignment of the C domains of IC-RFX and other mammalian RFX proteins and the *C. elegans* RFX protein daf-19. A consensus sequence is shown at the bottom of each alignment. Boxed and shaded residues define broadly conserved residues.

FIG. 8 illustrates an amino acid sequence alignment of the dimerization domains of IC-RFX and other mammalian RFX proteins and the *C. elegans* RFX protein daf-19. A consensus sequence is shown at the bottom of each alignment. Boxed and shaded residues define broadly conserved residues.

DETAILED DESCRIPTION OF THE INVENTION

I. Introduction

Figure 1:
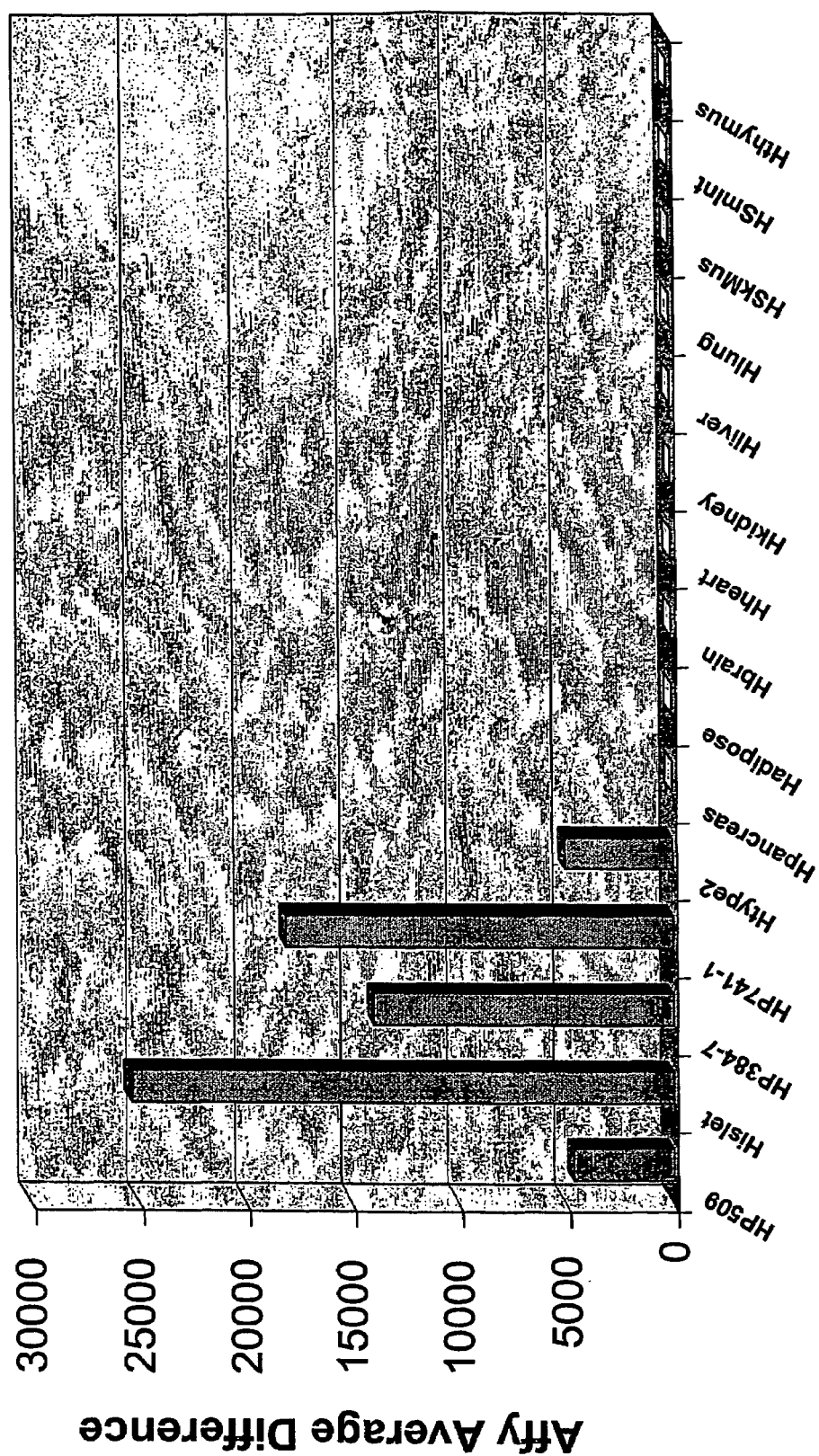
FIG. 1 illustrates that human IC-RFX is highly enriched in pancreatic islets as demonstrated by GeneChip data. Average Difference values from a survey of identical quantities of human tissue RNAs were obtained by hybridization of samples to a custom human islet Affymetrix GeneChip array. Probe set RD_BG02340, which detects IC-RFX transcripts, displays strong hybridization signals with human islet RNA samples from 5 separate donor pancreases (HP509, Hislet, HP384-7, HP741-1 and Htype2) but no hybridization signal to any of ten other human tissues (pancreas, adipose, brain, heart, kidney, liver, lung, skeletal muscle, small intestine or thymus).

The present application provides a novel islet-specific RFX transcription factor, designated IC-RFX, as well as methods and compositions useful for diagnosis and treatment of diabetes. Thus, the invention provides for diagnostic assays for detecting mutations in the IC-RFX gene, thereby diagnosing diabetics or those pre-disposed to develop diabetes. In addition, the invention provides for monitoring of expression of IC-RFX RNA or polypeptides.

Moreover, the invention provides for methods of supplementing IC-RFX expression in islets or other cells to promote differentiation of the cells into function beta-cells (i.e., insulin producing cells). The invention further provides for ex vivo supplementation or expression of IC-RFX in cells to promote beta cell differentiation prior to transplantation into a host.

IC-RFX also provides a useful target to screen for drugs for treating diabetes and increasing insulin production.

II. IC-RFX Expression in Cells and Induction of Insulin Production and Beta-Cell Differentiation Pancreatic beta-cells can be produced from non-beta cell pancreatic cells by providing for production of IC-RFX in a pancreatic cell either in vivo (e.g., by administration of an IC-RFX-encoding nucleic acid (e.g., RNA or DNA) to the pancreas of a subject, e.g., by introduction of nucleic acid into a lumen of a pancreatic duct), or in vitro, e.g., by contacting a target cell (e.g., an isolated, non-beta, pancreatic cell) with an IC-RFX-encoding nucleic acid (e.g., RNA or DNA) in culture (which cells can then be cultured, expanded, and transplanted into a subject). In some embodiments, other islet specific transcription factors such as neurogenin1, neurogenin2, neurogenin3, NeuroD1/BETA2, PDX-1, HNF4alpha, HNF4beta, HNF1alpha, nkx6.1, nkx2.2, isl-1, PAX6, Pax4, neuroD4, pbx-1, HB9, HNF6, HNF3b/FoxA2, or dimerization partners of IC-RFX, such as RFX1, RFX2, RFX3, RFX4 or RFX5, are also expressed in the same cell to induce differentiation and insulin production.

In one embodiment, beta cells are produced by providing for expression of IC-RFX at a level sufficient to induce a beta cell phenotype (e.g., glucose-dependent expression of insulin, glucokinase expression, etc.) in the target cell. Expression of IC-RFX in the target cell can be accomplished in a variety of ways. For example, in one embodiment, IC-RFX expression is accomplished by introduction of an IC-RFX-encoding nucleic acid (e.g., DNA or RNA) to provide for expression of the encoded IC-RFX polypeptide in the target cell). In another embodiment, IC-RFX expression is induced by introduction of a gene encoding a protein that provides for induction of IC-RFX expression (e.g., expression of an "upstream" positive regulator of IC-RFX expression in the target cell). In another embodiment, IC-RFX expression is accomplished by introduction of a gene encoding a protein that inhibits activity (e.g., function or expression) a negative regulator of IC-RFX expression. In another embodiment, IC-RFX expression is induced by introduction of a small molecule that provides for induction of IC-RFX expression (e.g., a small molecule pharmaceutical that induces IC-RFX expression in the target cell). In addition, production of pancreatic beta cells of the invention can also be accomplished by providing for production of factors induced by IC-RFX.

Where the IC-RFX nucleic acid to be delivered is DNA, any construct having a promoter (e.g., a promoter that is functional in a eukaryotic cell) operably linked to a DNA of interest can be used in the invention. Constructs for use in the invention may be any eukaryotic expression construct containing the IC-RFX DNA or RNA sequence of interest. Typically, the construct is capable of replication in eukaryotic and/or prokaryotic hosts (viruses in eukaryotic, plasmids in prokaryotic), which constructs are known in the art and are commercially available.

The constructs can be prepared using techniques well known in the art. Likewise, techniques for obtaining expression of exogenous DNA or RNA sequences in a genetically altered host cell are known in the art (see, for example, Kormal et al., *Proc. Natl. Acad. Sci. USA,* 84:2150-2154 (1987); Sambrook et al. MOLECULAR CLONING: A LABORATORY MANUAL, 2nd Ed., (1989).

In one embodiment, the DNA construct contains a promoter to facilitate expression of the DNA of interest within a pancreatic cell. The promoter can be a strong, viral promoter that functions in eukaryotic cells, e.g., a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521-530 919850) and the promoter from the long terminal repeat (LTR) of RSV (Gorman et al., *Proc. Natl. Acad. Sci. USA* 79:6777-6781 (1982)).

Alternatively, the promoter used may be a strong general eukaryotic promoter such as the actin gene promoter. In one embodiment, the promoter used may be a tissue-specific promoter. For example, the promoter used in the construct may be a pancreas specific promoter, a duct cell specific promoter or a stem cell specific promoter. In addition to promoters, the constructs of the invention can include sequences that enhance expression in the target cells. In another embodiment, the promoter is a regulated promoter, such as a tetracycline-regulated promoter, expression from which can be regulated by exposure to an exogenous substance (e.g., tetracycline).

The constructs can also comprise other components such as a marker (e.g., an antibiotic resistance gene (such as an ampicillin resistance gene) or β-galactosidase) to aid in selection or identification of cells containing and/or expressing the construct, an origin of replication for stable replication of the construct in a bacterial cell (preferably, a high copy number origin of replication), a nuclear localization signal, or other elements which facilitate production of the DNA construct, the protein encoded, or both.

For eukaryotic expression, the construct can contain a eukaryotic promoter operably linked to a DNA of interest, which is in turn operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. The construct may also include one or more introns, where appropriate, which can increase levels of expression of the DNA of interest, particularly where the DNA of interest is a cDNA (e.g., contains no introns of the naturally-occurring sequence). Any of a variety of introns known in the art may be used.

In an alternative embodiment, the nucleic acid delivered to the cell is an RNA encoding an IC-RFX polypeptide. In this embodiment, the RNA is adapted for expression (i.e., translation of the RNA) in a target cell. Methods for production of RNA (e.g., mRNA) encoding a protein of interest are well known in the art, and can be readily applied to produce RNA encoding IC-RFX polypeptides of the invention.

Delivery of IC-RFX nucleic acids can be accomplished using a viral or a non-viral vector. In one embodiment the nucleic acid is delivered within a viral particle, such as an adenovirus. In another embodiment, the nucleic acid is delivered in a formulation comprising naked DNA admixed with an adjuvant such as viral particles (e.g., adenovirus) or cationic lipids or liposomes. The precise vector and vector formulation used will depend upon several factors, such as the size of the DNA to be transferred, the delivery protocol to be used, and the like.

In general, viral vectors used in accordance with the invention are composed of a viral particle derived from a naturally-occurring virus which has been genetically altered to render the virus replication-defective and to deliver a recombinant gene of interest for expression in a target cell in accordance with the invention.

Numerous viral vectors are well known in the art, including, for example, retrovirus, adenovirus, adeno-associated virus, herpes simplex virus (HSV), cytomegalovirus (CMV), vaccinia and poliovirus vectors. Adenovirus and AAV are usually preferred viral vectors since these viruses efficiently infect slowly replicating and/or terminally differentiated cells. The viral vector may be selected according to its preferential infection of the cells targeted.

Where a replication-deficient virus is used as the viral vector, the production of infectious virus particles containing either DNA or RNA corresponding to the DNA of interest can be achieved by introducing the viral construct into a recombinant cell line that provides the missing components essential for viral replication. In one embodiment, transformation of the recombinant cell line with the recombinant viral vector will not result in production or substantial production of replication-competent viruses. Methods for production of replication-deficient viral particles containing a nucleic acid of interest are well known in the art and are described in, for example, Rosenfeld et al., Science 252:431-434 (1991) and Rosenfeld et al., Cell 68:143-155 (1992; U.S. Pat. No. 5,139, 941; U.S. Pat. No. 4,861,719; and U.S. Pat. No. 5,356,806. Methods and materials for manipulation of the mumps virus genome, characterization of mumps virus genes responsible for viral fusion and viral replication, and the structure and sequence of the mumps viral genome are described in Tanabayashi et al., *J. Virol.* 67:2928-2931 (1993); Takeuchi et al., *Archiv. Virol.*, 128:177-183 (1993); Tanabayashi et al., *Virol.* 187:801-804 (1992); Kawano et al., *Virol.*, 179:857-861 (1990); Elango et al., *J. Gen. Virol.* 69:2893-28900 (1988).

The nucleic acid of interest can also be introduced into a cell using a non-viral vector. Non-viral vectors include naked DNA (e.g., DNA not contained within a viral particle, and free of a carrier molecules such as lipids), chemical formulations comprising naked nucleic acid (e.g., a formulation of DNA (and/or RNA) and cationic compounds (e.g., dextran sulfate, cationic lipids)), and naked nucleic acid mixed with an adjuvant such as a viral particle (e.g., the DNA of interest is not contained within the viral particle, but the formulation is composed of both naked DNA and viral particles (e.g., adenovirus particles).

Alternatively or in addition, the nucleic acid can be complexed with polycationic substances such as poly-L-lysine or DEAC-dextran, targeting ligands, and/or DNA binding proteins (e.g., histones). DNA- or RNA-liposome complex formulations comprise a mixture of lipids which bind to genetic material (DNA or RNA) and facilitate delivery of the nucleic acid into the cell. Liposomes which can be used in accordance with the invention include DOPE (dioleyl phosphatidyl ethanol amine), CUDMEDA (N-(5-cholestrum-3-β-ol 3-urethanyl)-N',N'-dimethylethylene diamine).

The nucleic acid of interest can also be administered as a chemical formulation of DNA or RNA coupled to a carrier molecule (e.g., an antibody or a receptor ligand), which facilitates delivery to host cells for the purpose of altering the biological properties of the host cells. Chemical formulations include modifications of nucleic acids that allow coupling of the nucleic acid compounds to a carrier molecule such as a protein or lipid, or derivative thereof. Exemplary protein carrier molecules include antibodies specific to the cells of a targeted pancreatic cell or receptor ligands, e.g., molecules capable of interacting with receptors associated with a cell of a targeted pancreatic cell.

Nucleic acid encoding an IC-RFX polypeptide can be introduced into a cell in vitro to provide for at least transient expression. The cells into which the nucleic acid is introduced can be differentiated epithelial cells (e.g., pancreatic cells, gut cells, hepatic cells or duct cells), pluripotent adult or embryonic stem cells, or any mammalian cell capable of developing into β-cells or cells capable of expression of insulin in vitro following expression of an IC-RFX-encoding nucleic acid. The cell is subsequently implanted into a subject having a disorder characterized by a deficiency in insulin (e.g., diabetes), which disorder is amenable to treatment by islet cell replacement therapy. In some embodiments, the transfected host cell implanted in the subject is derived from the individual who will receive the transplant (e.g., to provide an autologous transplant). For example, in a subject having Type 1 diabetes, pluripotent stem cells, hepatic cells, gut cells or pancreatic cells can be isolated from the affected subject, the cells modified to express IC-RFX-encoding DNA, and the cells implanted in the affected subject to provide for insulin production, or the transformed cells cultured so as to facilitate development of the cells into insulin-producing β-cells. Alternatively, pluripotent stem cells, hepatic cells, gut cells or pancreatic cells from another subject (the "donor") could be modified to express IC-RFX-encoding DNA, and the cells subsequently implanted in the affected subject to provide for insulin production, or the transformed cells cultured so as to facilitate development of the cells into insulin-producing .beta.-cells.

Introduction of nucleic acid into the cell in vitro can be accomplished according to methods well known in the art (e.g., through use of electroporation, microinjection, lipofection infection with a recombinant (preferably replication-deficient) virus, and other means well known in the art). The nucleic acid is generally operably linked to a promoter that facilitates a desired level of polypeptide expression (e.g., a promoter derived from CMV, SV40, adenovirus, or a tissue-specific or cell type-specific promoter). Transformed cells containing the recombinant nucleic acid can be selected and/or enriched via, for example, expression of a selectable marker gene present in the introduced construct or that is present on a nucleic acid that is co-transfected with the construct. Typically selectable markers provide for resistance to antibiotics such as tetracycline, hygromycin, neomycin, and the like. Other markers can include thymidine kinase and the like. Other markers can include markers that can be used to identify expressing cells, such as beta-galactosidase or green florescent protein.

Expression of the introduced nucleic acid in the transformed cell can be assessed by various methods known in the art. For example, expression of the introduced gene can be examined by Northern blot to detect mRNA that hybridizes with a DNA probe derived from the relevant gene. Those cells that express the desired gene can be further isolated and expanded in in vitro culture using methods well known in the art. The host cells selected for transformation will vary with the purpose of the ex vivo therapy (e.g., insulin production), the site of implantation of the cells, and other factors that will vary with a variety of factors that will be appreciated by the ordinarily skilled artisan.

The transformed cell can also be examined for the development of an islet cell phenotype. For example, expression of insulin could be detected by PCR, northern blot, immunocytochemistry, western blot, or ELISA. Alternatively a marker gene such as green florescent protein or an antibiotic resistance gene operatively linked to an islet specific promoter such as the insulin gene promoter could be used for identification or selection of differentiated islet cells. Methods for engineering a host cell for expression of a desired gene product(s) and implantation or transplantation of the engineered cells (e.g., ex vivo therapy) are known in the art. See, e.g., Gilbert et al. *Transplantation* 56:423-427 (1993). For expression of a desired gene in exogenous or autologous cells and implantation of the cells (e.g., islet cells) into pancreas, see, e.g., Docherty, *Clin Sci* (Colch) 92:321-330 (1997); Hegre et al., *Acta Endocrinol Suppl* (*Copenh*) 205:257-281 (1976); Sandler et al., *Transplantation* 63:1712-1718 (1997); Calafiore, *Diabetes Care* 20:889-896 (1997); Kenyon et al., *Diabetes Metab Rev* 12:361-372 (1996); Chick et al. *Science* 197:780-782 (1977). In general, the cells can be implanted into the pancreas, or to any practical or convenient site, e.g., subcutaneous site, liver, peritoneum.

In general, after expansion of the transformed cells in vitro, the cells are implanted into the mammalian subject by methods well known in the art. The number of cells implanted is a number of cells sufficient to provide for expression of levels of insulin sufficient to lower blood glucose levels. The number of cells to be transplanted can be determined based upon such factors as the levels of polypeptide expression achieved in vitro, and/or the number of cells that survive implantation. The transformed cells are implanted in an area of dense vascularization such as the liver, and in a manner that minimizes surgical intervention in the subject. The engraftment of the implant of transformed cells is monitored by examining the mammalian subject for classic signs of graft rejection, i.e., inflammation and/or exfoliation at the site of implantation, and fever, and by monitoring blood glucose levels.

The transplantation method described above is not limited to the expression of IC-RFX. Engineering a host cell for expression of additional transcription factors, such as islet-specific transcription factors (e.g., neurogenin1, neurogenin2, neurogenin3, NeuroD1/BETA2, PDX-1, HNF4alpha, HNF4beta, HNF1alpha, nkx6.1, nkx2.2, isl-1, PAX6, Pax4, neuroD4, pbx-1, HB9, HNF6, HNF3b/FoxA2), or dimerization partners of IC-RFX (such as RFX1, RFX2, RFX3, RFX4 or RFX5) may be beneficial to subjects with insulin deficiencies.

IC-RFX-encoding nucleic acids can be delivered directly to a subject to provide for IC-RFX expression in a target cell (e.g., a pancreatic cell, gut cell, liver cell, or other organ cell capable of expressing an IC-RFX transcription factor and providing production of insulin), thereby promoting development of the cell into an insulin-producing cell (e.g., in pancreas) or to cure a defect in transcription factor expression in the subject. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, or pneumatic injection using a gene gun).

In general terms, the delivery method comprises introducing a nucleic acid into a pancreatic cell. For example, the nucleic acid of interest can be provided in either a viral or non-viral vector (including naked DNA) that is introduced into the pancreas in vivo via the duct system. Intraductal administration can be accomplished by cannulation by, for example, insertion of the cannula through a lumen of the gastrointestinal tract, by insertion of the cannula through an external orifice, or insertion of the cannula through the common bile duct. Retrograde ductal administration may be accomplished in the pancreas by endoscopic retrograde chalangio-pancreatography (ECRP). Exemplary methods for accomplishing intraductal delivery to the pancreas are described in U.S. Pat. No. 6,004,944.

The precise amount of IC-RFX-encoding nucleic acid administered will vary greatly according to a number of factors including the susceptibility of the target cells to transformation, the size and weight of the subject, the levels of protein expression desired, and the condition to be treated. The amount of nucleic acid and/or the number of infectious viral particles effective to infect the targeted tissue, transform a sufficient number of cells, and provide for production of a desired level of insulin can be readily determined based upon such factors as the efficiency of the transformation in vitro and the susceptibility of the targeted cells to transformation. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Pancreatic cells modified according to the invention can facilitate sufficiently high levels of expression of a nucleic acid of interest, particularly where the nucleic acid delivered is DNA and the DNA of interest is operably linked to a strong eukaryotic promoter (e.g., CMV, MMTV). The expressed protein can induce islet cell and insulin production. Thus the methods of the invention are useful in treating a mammalian subject having a variety of insulin related conditions.

The actual number of transformed pancreatic cells required to achieve therapeutic levels of the protein of interest will vary according to several factors including the protein to be expressed, the level of expression of the protein by the transformed cells, the rate in which the protein induces islet cell production (in particular β-cells), and the condition to be treated.

Regardless of whether the IC-RFX-encoding nucleic acid is introduced in vivo or ex vivo, the nucleic acid (or islet cells produced in vitro or recombinant cells expressing the IC-RFX nucleic acid that are to be transplanted for development into islet cells in vivo post-transplantation) can be administered in combination with other genes and other agents The effects of ex vivo or in vivo therapy according to the methods of the invention can be monitored in a variety of ways. Generally, a sample of blood from the subject can be assayed for, for example, levels of glucose, proinsulin, c-peptide, and insulin. Appropriate assays for detecting proinsulin, c-peptide, insulin and glucose in blood samples are well known in the art. Evidence for recurrent autoimmunity can be gauged by assaying for autoreactive T cells or for antibodies against islet proteins such as glutamic acid decarboxylase (GAD), or other autoantigens well known in the art.

III. General Recombinant Nucleic Acid Methods for Use with the Invention

In numerous embodiments of the present invention, nucleic acids encoding an IC-RFX polypeptide of the present invention will be isolated and cloned using recombinant methods. Such embodiments are used, e.g., to isolate polynucleotides identical or substantially identical to SEQ ID NO:1 for protein expression or during the generation of variants, derivatives, expression cassettes, or other sequences derived from an polypeptide or polynucleotide of the invention, to monitor gene expression, for the isolation or detection of sequences in different species, for diagnostic purposes in a patient, e.g., to detect mutations in a polypeptide or polynucleotide of the invention or to detect expression levels of nucleic acids or polypeptides. In some embodiments, the sequences encoding the polypeptides of the invention are operably linked to a heterologous promoter. In one embodiment, the nucleic acids of the invention are from any mammal, including, in particular, e.g., a human, a mouse, a rat, etc.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

The sequence of the cloned genes and synthetic oligonucleotides can be verified after cloning using, e.g., the chain termination method for sequencing double-stranded templates of Wallace et al., *Gene* 16:21-26 (1981).

In general, the nucleic acids encoding IC-RFX polypeptides are cloned from DNA sequence libraries that are made to encode cDNA or genomic DNA. The particular sequences can be located by hybridizing with an oligonucleotide probe, the sequence of which can be derived from the sequences disclosed herein, which provide a reference for PCR primers and defines suitable regions for isolating probes pecific for the polypeptides or polynucleotides of the invention. Alternatively, where the sequence is cloned into an expression library, the expressed recombinant protein can be detected immunologically with antisera or purified antibodies made against a polypeptide of interest, including those disclosed herein.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra).

Briefly, to make the cDNA library, one should choose a source that is rich in the desired cDNA, e.g., pancreatic or islet cells. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific sequences disclosed herein. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying the genes encoding a polypeptide of the invention from mammalian tissues can be derived from the sequences provided herein. For a general overview of PCR, see, Innis et al. *PCR Protocols: A Guide to Methods and Applications,* Academic Press, San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A polynucleotide encoding a polypeptide of the invention can be cloned using intermediate vectors before transformation into mammalian cells for expression. These intermediate vectors are typically prokaryote vectors or shuttle vectors. The proteins can be expressed in either prokaryotes or eukaryotes, using standard methods well known to those of skill in the art.

Expression cassettes comprising a promoter operably linked to a polynucleotide encoding an IC-RFX polypeptide can be constructed with standard molecular methods. In some cases, the promoter is heterologous to the polynucleotide.

IV. Purification of Proteins of the Invention

Either naturally occurring or recombinant polypeptides of the invention can be purified for use in functional assays. Naturally occurring polypeptides of the invention can be purified from any source (e.g., from islet cells or other tissues expressing IC-RFX). Recombinant polypeptides can be purified from any suitable expression system.

The polypeptides of the invention may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant polypeptides are being purified. For example, proteins having established molecular adhesion properties can be reversibly fused to a polypeptide of the invention. With the appropriate ligand, either protein can be selectively adsorbed to a purification column and then freed from the column in a relatively pure form. The fused protein may be then removed by enzymatic activity. Finally polypeptides can be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Purification of Proteins from Insect Cells

Proteins can also be purified from eukaryotic gene expression systems as described in, e.g., Fernandez and Hoeffler, *Gene Expression Systems* (1999). In some embodiments, baculovirus expression systems are used to isolate proteins of the invention. Recombinant baculoviruses are generally generated by replacing the polyhedrin coding sequence of a baculovirus with a gene to be expressed (e.g., encoding a polypeptide of the invention). Viruses lacking the polyhedrin gene have a unique plaque morphology making them easy to recognize. In some embodiments, a recombinant baculovirus is generated by first cloning a polynucleotide of interest into a transfer vector (e.g., a pUC based vector) such that the polynucleotide is operably linked to a polyhedrin promoter. The transfer vector is transfected with wildtype DNA into an insect cell (e.g., Sf9, Sf21 or BT1-TN-5B1-4 cells), resulting in homologous recombination and replacement of the polyhedrin gene in the wildtype viral DNA with the polynucleotide of interest. Virus can then be generated and plaque purified. Protein expression results upon viral infection of insect cells. Expressed proteins can be harvested from cell supernatant if secreted, or from cell lysates if intracellular. See, e.g., Ausubel et al. and Fernandez and Hoeffler, supra.

C. Standard Protein Separation Techniques For Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine (His), glutathione S transferase (GST) and the like can be used to purify polypeptides. The His tag will also act as a chelating agent for certain metals (e.g., Ni) and thus the metals can also be used to purify His-containing polypeptides. After purification, the tag is optionally removed by specific proteolytic cleavage.

It will be apparent to one of skill that chromatographic techniques can be performed at any scale and using equipment from many different manufacturers (e.g., Pharmacia Biotech).

V. Detection of Polynucleotides of the Invention

Those of skill in the art will recognize that detection of expression of polynucleotides and polypeptides of the invention has many uses. For example, as discussed herein, detection of levels of polynucleotides and polypeptides of the invention in a patient is useful for diagnosing diabetes or a predisposition for at least some of the pathological effects of diabetes. In addition, at least some familial diabetes can be diagnosed by detecting the IC-RFX allele in an individual. Moreover, detection of gene expression is useful to identify modulators of expression of polynucleotides and polypeptides of the invention.

A variety of methods of specific DNA and RNA measurement that use nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention. In some cases, a polynucleotide from a subject is isolated (e.g., by PCR amplification) and sequenced to detect mutations (e.g., deletions, insertions, point mutations).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

The amount of, for example, an RNA is measured by quantifying the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), i.e. Gene Chips or microarrays, available from Affymetrix, Inc. in Santa Clara, Calif. can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759. Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in temms of expression levels of particular genes and can be correlated with a particular disease or condition or treatment. See, e.g., Schena et al., *Science* 270: 467-470 (1995) and Lockhart et al., *Nature Biotech.* 14: 1675-1680 (1996).

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulavski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *PNAS* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed) *Fundamental Immunology, Third Edition* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1989); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

An alternative means for determining the level of expression of the nucleic acids of the present invention is in situ hybridization. In situ hybridization assays are well known and are generally described in Angerer et al., *Methods Enzymol.* 152:649-660 (1987). In an ill situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

VI. Immunological Detection of Polypeptides of the Invention

In addition to the detection of IC-RFX polynucleotides of the invention and gene expression using nucleic acid hybridization technology, one can also use immunoassays to detect polypeptides of the invention. Immunoassays can be used to qualitatively or quantitatively analyze polypeptides of the invention. A general overview of the applicable technology can be found in Harlow & Lane, *Antibodies: A Laboratory Manual* (1988).

A. Antibodies to Target Proteins or Other Immunogens

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature,* 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein is conjugated to a carrier protein and used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their crossreactivity against proteins other than the polypeptides of the invention or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to polypeptides of the invention. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells according to the general protocol outlined by Huse et al., supra.

Once target immunogen-specific antibodies are available, the immunogen can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to full-length polypeptides of the invention or a fragment thereof. This antiserum is selected to have low cross-reactivity against other proteins and any such cross-reactivity is removed by immunoabsorption prior to use in the immunoassay.

B. Immunological Binding Assays

In some embodiments, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume 37: Antibodies in Cell Biology*, Academic Press, Inc. NY (1993); Stites, supra. Immunological binding assays (or immunoassays) typically utilize a "capture agent" to specifically bind to and often immobilize the analyte (e.g., full-length polypeptides of the present invention, or antigenic subsequences thereof). The capture agent is a moiety that specifically binds to the analyte. The antibody may be produced by any of a number of means well known to those of skill in the art and as described above.

Immunoassays also often utilize a labeling agent to bind specifically to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of *streptococcal* bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins or analytes of interest from tissue samples may be either competitive or noncompetitive. Noncompetitive immunoassays are assays in which the amount of captured protein or analyte is directly measured. In one preferred "sandwich" assay, for example, the capture agent (e.g., antibodies specific for the polypeptides of the invention) can be bound directly to a solid substrate where it is immobilized. These immobilized antibodies then capture the polypeptide present in the test sample. The polypeptide of the invention thus immobilized is then bound by a labeling agent, such as a second labelled antibody specific for the polypeptide. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of protein or analyte present in the sample is measured indirectly by measuring the amount of an added (exogenous) protein or analyte displaced (or competed away) from a specific capture agent (e.g., antibodies specific for a polypeptide of the invention) by the protein or analyte present in the sample. The amount of immunogen bound to the antibody is inversely proportional to the concentration of immunogen present in the sample. In a particularly preferred embodiment, the antibody is immobilized on a solid substrate. The amount of analyte may be detected by providing a labeled analyte molecule. It is understood that labels can include, e.g., radioactive labels as well as peptide or other tags that can be recognized by detection reagents such as antibodies.

Immunoassays in the competitive binding format can be used for cross-reactivity determinations. For example, the protein encoded by the sequences described herein can be immobilized on a solid support. Proteins are added to the assay and compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In some embodiments, western blot (immunoblot) analysis is used to detect and quantify the presence of a polypeptide of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, antibodies are selected that specifically bind to the polypeptides of the invention on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

VII. Identification of Modulators of Polypeptides of the Invention

Modulators of a IC-RFX polypeptide of the invention, i.e. agonists or antagonists of an IC-RFX polypeptide's activity, or an IC-RFX polypeptide's or an IC-RFX polynucleotide's expression, are useful for treating a number of human diseases, including diabetes. For example, administration of modulators can be used to treat diabetic patients or prediabetic individuals to prevent progression, and therefore symptoms, associated with diabetes.

A. Agents that Modulate Polypeptides of the Invention

The agents tested as modulators of polypeptides of the invention can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Modulators also include agents designed to reduce the level of mRNA encoding a polypeptide of the invention (e.g. antisense molecules, ribozymes, DNAzymes, small inhibitory RNAs and the like) or the level of translation from an mRNA (e.g., translation blockers such as an antisense molecules that are complementary to translation start or other sequences on an mRNA molecule). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" sucb as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Methods of Screening for Modulators of the Polypeptides of the Invention

A number of different screening protocols can be utilized to identify agents that modulate the level of expression or activity of a polynucleotide of a polypeptide of the invention in cells, particularly mammalian cells, and especially human cells. In general terms, the screening methods involve screening a plurality of agents to identify an agent that modulates the activity of a polypeptide of the invention by, e.g., binding to the polypeptide, preventing an inhibitor or activator from binding to the polypeptide, increasing association of an inhibitor or activator with the polypeptide, or activating or inhibiting expression of the polypeptide.

Any cell expressing a full-length polypeptide of the invention or a fragment thereof can be used to identify modulators. In some embodiments, the cells are eukaryotic cells lines (e.g., CHO or HEK293) transformed to express a heterologous polypeptide of the invention. In some embodiments, a cell expressing an endogenous polypeptide of the invention is used in screens. In other embodiments, modulators are screened for their ability to effect insulin production of a cell or to induce other β-cell phenotypes in a cell.

1. Polypeptide Binding Assays

Preliminary screens can be conducted by screening for agents capable of binding to polypeptides of the invention, as at least some of the agents so identified are likely modulators of a polypeptide of the invention. Binding assays are also useful, e.g., for identifying endogenous proteins that interact with polypeptides of the invention. For example, antibodies, receptors or other molecules that bind polypeptides of the invention can be identified in binding assays.

Binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on nondenaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89). Other binding assays involve the use of mass spectrometry or NMR techniques to identify molecules bound to a polypeptide of the invention or displacement of labeled substrates. The polypeptides of the invention utilized in such assays can be naturally expressed, cloned or synthesized.

In addition, mammalian or yeast two-hybrid approaches (see, e.g., Bartel, P. L. et. al. *Methods Enzymol,* 254:241 (1995)) can be used to identify polypeptides or other molecules that interact or bind when expressed together in a host cell.

2. Polypeptide Activity

The activity of polypeptides of the invention can be assessed using a variety of in vitro and in vivo assays to determine functional, chemical, and physical effects, e.g., measuring ligand binding (e.g., radioactive or otherwise labeled ligand binding), second messengers (e.g., cAMP, cGMP, $IP_3$, DAG, or $Ca^{2+}$), ion flux, phosphorylation levels, transcription levels, and the like. Furthermore, such assays can be used to test for inhibitors and activators of the polypeptides of the invention. Modulators can also be genetically altered versions of polypeptides of the invention.

The polypeptide of the assay will be selected from a polypeptide with substantial identity to a sequence of SEQ ID NO:2, or other conservatively modified variants thereof. Generally, the amino acid sequence identity will be at least 70%, optionally at least 85%, optionally at least 90-95% to the polypeptides exemplified herein. Optionally, the polypeptide of the assays will comprise a fragment of a polypeptide of the invention, such as an extracellular domain, transmembrane domain, cytoplasmic domain, ligand binding domain, subunit association domain, active site, and the like. Either a polypeptide of the invention or a domain thereof can be covalently linked to a heterologous protein to create a chimeric protein used in the assays described herein.

Modulators of polypeptide activity are tested using either recombinant or naturally occurring polypeptides of the invention. The protein can be isolated, expressed in a cell, expressed in a membrane derived from a cell, expressed in tissue or in an animal, either recombinant or naturally occurring. For example, tissue slices, dissociated cells, e.g., from tissues expressing polypeptides of the invention, transformed cells, or membranes can be used. Modulation is tested using one of the in vitro or in vivo assays described herein.

Modulator binding to polypeptides of the invention, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index), hydrodynamic (e.g., shape), chromatographic, or solubility properties.

Samples or assays that are treated with a potential modulator (e.g., a "test compound") are compared to control samples without the test compound, to examine the extent of modulation. Control samples (untreated with activators or inhibitors) are assigned a relative activity value of 100. Inhibition of the polypeptides of the invention is achieved when the activity value relative to the control is about 90%, optionally 50%, optionally 25-0%. Activation of the polypeptides of the invention is achieved when the activity value relative to the control is 110%, optionally 150%, 200%, 300%, 400%, 500%, or 1000-2000%.

3. Expression Assays

Screening for a compound that modulates the expression of a polynucleotide or a polypeptide of the invention is also provided. Screening methods generally involve conducting cell-based assays in which test compounds are contacted with one or more cells expressing a polynucleotide or a polypeptide of the invention, and then detecting an increase or decrease in expression (either transcript or translation product). Assays can be performed with any cells that express a polynucleotide or a polypeptide of the invention.

Expression can be detected in a number of different ways. As described infra, the expression level of a polynucleotide of the invention in a cell can be determined by probing the mRNA expressed in a cell with a probe that specifically hybridizes with a transcript (or complementary nucleic acid derived therefrom) of a polynucleotide of the invention. Probing can be conducted by lysing the cells and conducting Northern blots or without lysing the cells using in situ-hybridization techniques. Alternatively, a polypeptide of the invention can be detected using immunological methods in which a cell lysate is probed with antibodies that specifically bind to the polypeptide.

The level of expression or activity of a polynucleotide or a polypeptide of the invention can be compared to a baseline value. The baseline value can be a value for a control sample or a statistical value that is representative of expression levels of a polynucleotide or a polypeptide of the invention for a control population (e.g., lean non-diabetic individuals) or cells (e.g., normal β-cells that produce insulin). As a negative control, expression levels can also be determined for cells that do not express the polynucleotide or a polypeptide of the invention. Such cells generally are otherwise substantially genetically identical to the test cells.

A variety of different types of cells can be utilized in the reporter assays. Cells that do not endogenously express a polypeptide of the invention can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HEK293, HepG2, COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

4. Validation

Agents that are initially identified by any of the foregoing screening methods can be further tested to validate the apparent activity. Modulators that are selected for further study can be tested for an effect on insulin levels in animals.

For example, the effect of the compound can be assessed in diabetic animals. The blood glucose and insulin levels can be determined. The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty rats etc) or polygenic models of diabetes (e.g., OLETF rats, GK rats, NSY mice, and KK mice) can be useful for validating modulation of a polypeptide of the invention in a diabetic or insulin resistant animal. In addition, transgenic animals expressing human polypeptides of the invention can be used to further validate drug candidates.

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

A molecule of interest (e.g., a polypeptide or polynucleotide of the invention, or a modulator thereof) can be bound to the solid-state component, directly or indirectly, via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, poly-His, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to those of skill in the art. For example, poly(ethelyne glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of a polypeptide of the invention. Control reactions that measure activity of a polypeptide of the invention in a cell in a reaction that does not include a potential modulator are optional, as the assays are highly uniform. Such optional control reactions are appropriate and increase the reliability of the assay. Accordingly, in some embodiments, the methods of the invention include such a control reaction. For each of the assay formats described, "no modulator" control reactions that do not include a modulator provide a background level of binding activity.

In some assays it will be desirable to have positive controls. At least two types of positive controls are appropriate. First, a known activator of a polypeptide or a polynucleotide of the invention can be incubated with one sample of the assay, and the resulting increase in signal resulting from an increased expression level or activity of a polypeptide or a polynucleotide of the invention are determined according to the methods herein. Second, a known inhibitor of a polypeptide or a polynucleotide of the invention can be added, and the resulting decrease in signal for the expression or activity of a polypeptide or a polynucleotide of the invention can be similarly detected. It will be appreciated that modulators can also be combined with activators or inhibitors to find modulators that inhibit the increase or decrease that is otherwise caused by the presence of the known modulator of a polypeptide or a polynucleotide of the invention.

VIII. Compositions, Kits and Integrated Systems

The invention provides compositions, kits and integrated systems for practicing the assays described herein using nucleic acids or polypeptides of the invention, antibodies, etc.

The invention provides assay compositions for use in solid phase assays; such compositions can include, for example, one or more nucleic acids encoding a polypeptide of the invention immobilized on a solid support, and a labeling reagent. In each case, the assay compositions can also include additional reagents that are desirable for hybridization. Modulators of expression or activity of a polypeptide of the invention can also be included in the assay compositions.

The invention also provides kits for carrying out the assays of the invention. The kits typically include a probe that comprises an antibody that specifically binds to a polypeptide of the invention or a polynucleotide sequence encoding such polypeptides, and a label for detecting the presence of the probe. The kits may include at least one polynucleotide sequence encoding a polypeptide of the invention. Kits can include any of the compositions noted above, and optionally further include additional components such as instructions to practice a high-throughput method of assaying for an effect on expression of the genes encoding a polypeptide of the invention, or on activity of a polypeptide of the invention, one or more containers or compartments (e.g., to hold the probe, labels, or the like), a control modulator of the expression or activity of a polypeptide of the invention, a robotic armature for mixing kit components or the like.

The invention also provides integrated systems for high-throughput screening of potential modulators for an effect on the expression or activity of a polypeptide of the invention. The systems can include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

IX. Administration and Pharmaceutical Compositions

Modulators of the polypeptides of the invention (e.g., antagonists or agonists) can be administered directly to the mammalian subject for modulation of activity of a polypeptide of the invention in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the a polypeptide of the invention, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

The modulators (e.g., agonists or antagonists) of the expression or activity of a polypeptide of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W., (ed.), *Current Therapy In Endocrinology And Metabolism*, 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Ann. J. Med.* (1995) 98: 443-451; and Iwamoto, Y. et al., *Diabet. Med.* (1996) 13 365-370; Kwiterovich, P. *Am. J. Cardiol* (1998) 82(12A): 3U-17U). These studies indicate that modulation of diabetes, among other diseases, can be further improved by the addition of a second agent to the therapeutic regimen. Combination therapy includes administration of a single pharmaceutical dosage formulation that contains a modulator of the invention and one or more additional active agents, as well as administration of a modulator and each active agent in its own separate pharmaceutical dosage formulation. For example, a modulator and a thiazolidinedione can be administered to the human subject together in a single oral dosage composition, such as a tablet or capsule, or each agent can be administered in separate oral dosage formulations. Where separate dosage formulations are used, a modulator and one or more additional active agents can be administered at essentially the same time (i.e., concurrently), or at separately staggered times (i.e., sequentially). Combination therapy is understood to include all these regimens.

One example of combination therapy can be seen in treating pre-diabetic individuals (e.g., to prevent progression into type 2 diabetes) or diabetic individuals (or treating diabetes and its related symptoms, complications, and disorders), wherein the modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No. 5,859, 037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose); amylin and amylin derivatives (such as pramlintide, (see, also, U.S. Pat. Nos. 5,902,726; 5,124,314; 5,175, 145 and 6,143,718.)); insulin secretogogues (such as repaglinide, gliquidone, and nateglinide (see, also, U.S. Pat. Nos. 6,251,856; 6,251,865; 6,221,633; 6,174,856)), and insulin.

XI. Diagnosis of Diabetes

The present invention also provides methods of diagnosing diabetes or a predisposition of at least some of the pathologies of diabetes. Diagnosis can involve determination of a genotype of an individual and comparison of the genotype with alleles known to have an association with the occurrence of diabetes. Alternatively, diagnosis also involves determining the level of a polypeptide or polynucleotide of the invention in a patient and then comparing the level to a baseline or range. Typically, the baseline value is representative of a polypeptide or polynucleotide of the invention in a healthy (e.g., non-diabetic lean) person.

Variation of levels (e.g., low or high levels) of a polypeptide or polynucleotide of the invention compared to the baseline range indicates that the patient is either diabetic or at risk of developing at least some of the pathologies of diabetes (e.g., pre-diabetic). The level of a polypeptide in a non-diabetic lean individual can be a reading from a single individual, but is typically a statistically relevant average from a group of lean individuals. The level of a polypeptide in a lean individual can be represented by a value, for example in a computer program.

In some embodiments, the baseline level and the level in a lean sample from an individual, or at least two samples from the same individual differ by at least about 5%, 10%, 20%, 50%, 75%, 100%, 150%, 200%, 300%, 400%, 500%, 1000% or more. In some embodiments, the sample from the individual is greater by at least one of the above-listed percentages relative to the baseline level. In some embodiments, the sample from the individual is lower by at least one of the above-listed percentages relative to the baseline level.

Glucose/insulin tolerance tests can also be used to detect the effect of glucose levels on levels of a polypeptide or polynucleotide of the invention. In glucose tolerance tests, the patient's ability to tolerate a standard oral glucose load is evaluated by assessing serum and urine specimens for glucose levels. Blood samples are taken before the glucose is ingested, glucose is given by mouth, and blood or urine glucose levels are tested at set intervals after glucose ingestion. Similarly, meal tolerance tests can also be used to detect the effect of insulin or food, respectively, on levels of a polypeptide or polynucleotide of the invention.

EXAMPLE

The following example is offered to illustrate, but not to limit the claimed invention.

Figure 4:
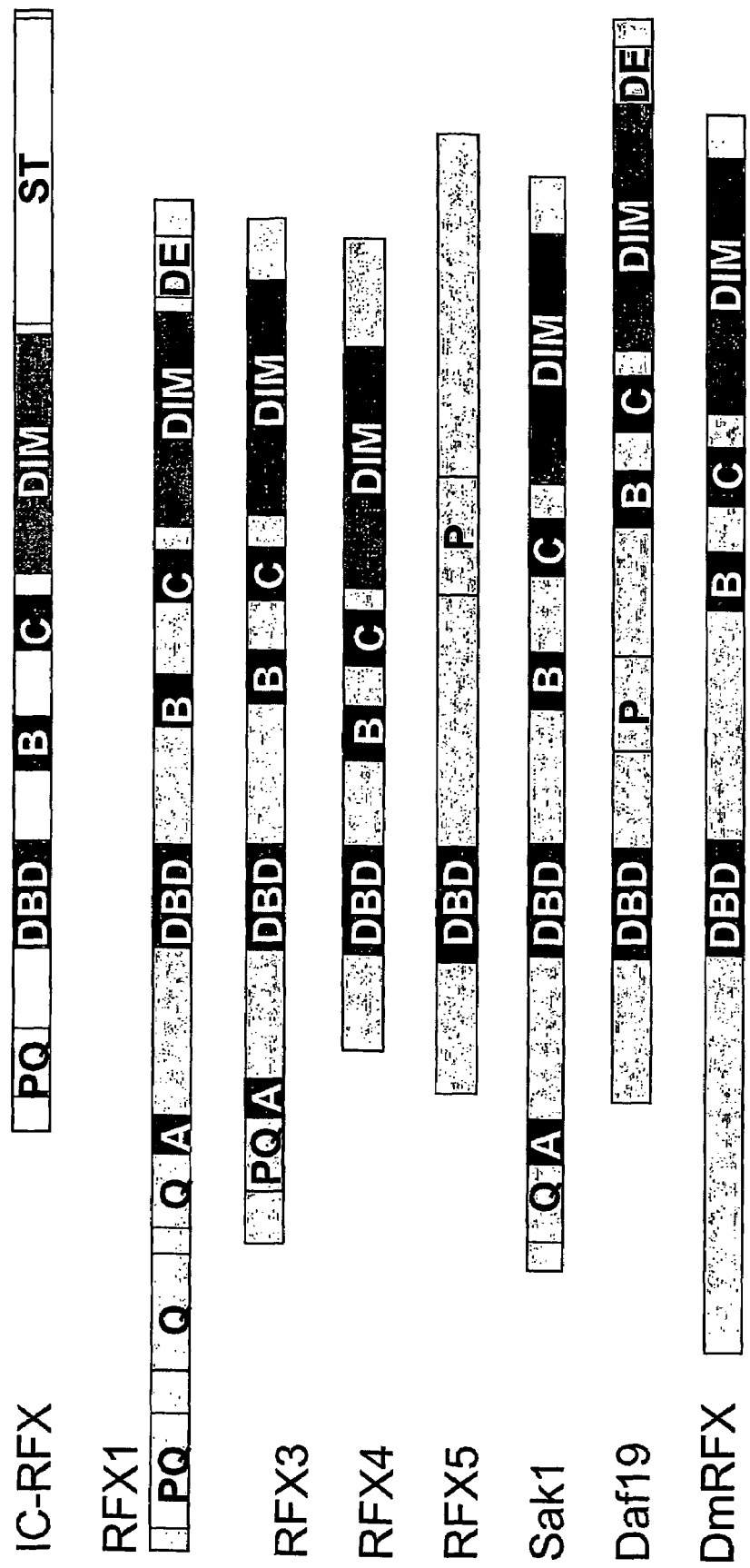
FIG. 4 provides a domain structure comparison of IC-RFX with other RFX proteins. DBD=DNA binding domain, DIM=dimerization domain, A, B and C designate conserved domains of unknown function, PQ=proline/glutamine-rich region, ST=serine/threonine-rich region, Q=glutamine-rich region, P=proline-rich region, and DE=glutamate/aspartate-rich region. Sak1 is the *S. pombe* RFX representative, Daf-19 is a *C. elegans* gene product, and DMRFX is a *Drosophila* RFX protein.

IC-RFX is a previously undescribed member of the RFX family that shares the conserved DNA binding domain (DBD) with the rest of the members of the RFX family (FIG. 4). IC-RFX also has conserved (with RFXs 1-4) dimerization, B and C domains. See, Emery P et al., *Nucleic Acids Res.* 24: 803-807 (1996) and FIGS. 5-8. There is no obvious A domain in IC-RFX. In this regard, IC-RFX most resembles RFX4 in domain organization (Morotomi-Yano K et al., *J. Biol. Chem.* 277: 836-842 (2002)). Indeed, the RFX4 DBD also has the greatest amino acid identity with that of IC-RFX (54/76 or 71%) (FIG. 5).

IC-RFX is also similar to the *C. elegans* RFX protein daf-19 in B, C, dimerization and DBD domains (45/76 or 59% identical in the DBD domain) and in overall domain organization. Daf-19 is specifically expressed in a subset of sensory neurons, and these neurons are absent in daf-19 null mutants. See, e.g., Swoboda P et al. *Mol Cell.* 5: 411-2(2000)). Daf-19 is the only RFX protein found in *C. elegans*. RFX1, 2, 3, 4, and 5 are all transcription factors that bind to conserved DNA sequences called X boxes in the promoters of the genes that they regulate (Sengupta K et al., *J. Biol. Chem.* 277: 24926-24937 (2002)).

Figure 2:
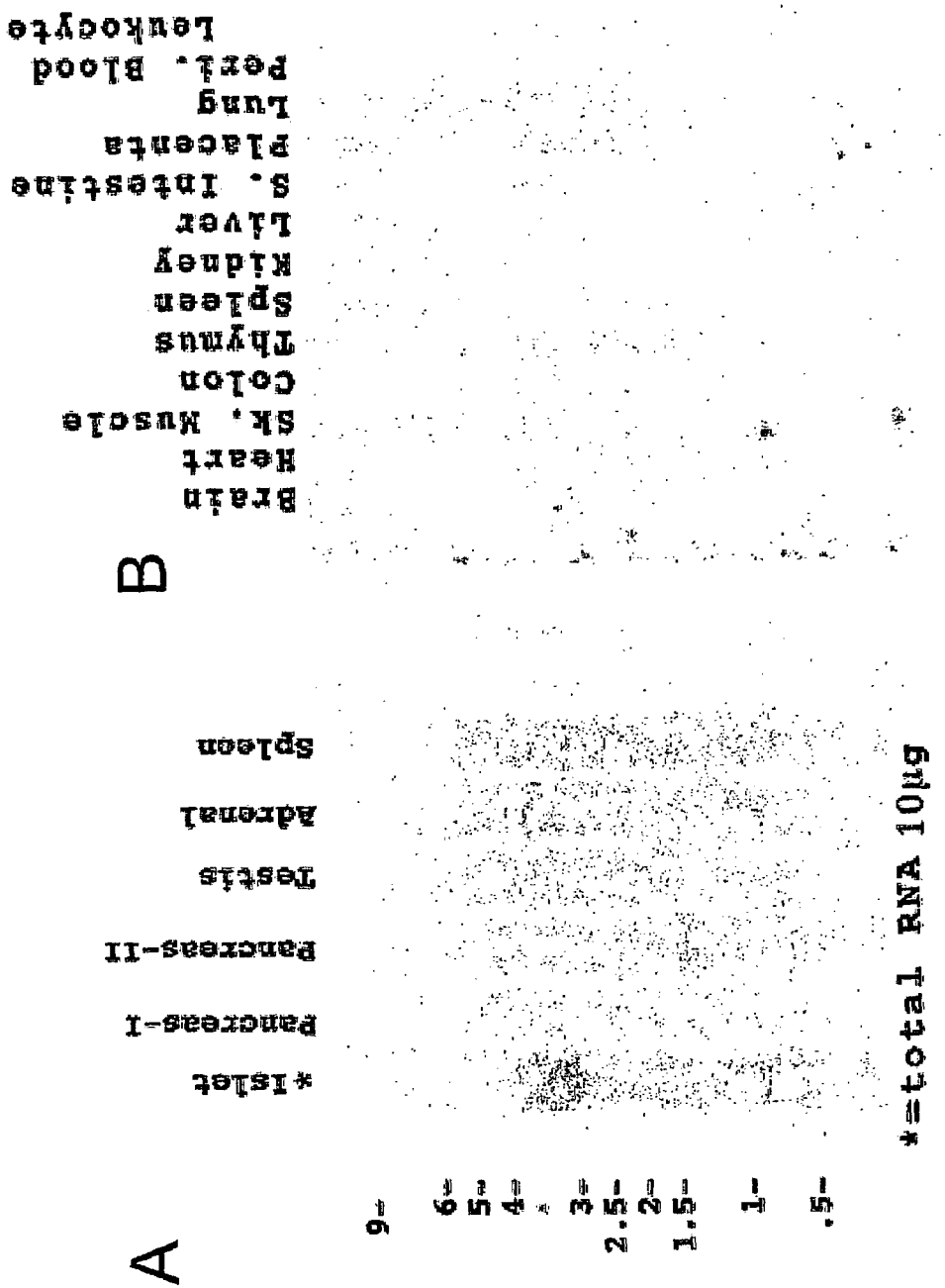
FIG. 2 illustrates that human IC-RFX is highly enriched in pancreatic islets as demonstrated by Northern blot. A $^{32}$P-labeled human IC-RFX cDNA probe hybridized with filters A and B simultaneously under identical conditions. Filter A is a blot of 10 µg of total RNA from a human islet sample along with 2 µg polyA+RNAs from two different human pancreas samples, as well as 2 µg samples of polyA+RNA from human testis, adrenal and spleen. Filter B is a commercial Multiple Tissue Northern blot (Clontech 2001 catalog #7780-1). A hybridizing transcript (approximately 3.3 kb) is found only in the human islet sample.
Figure 3:
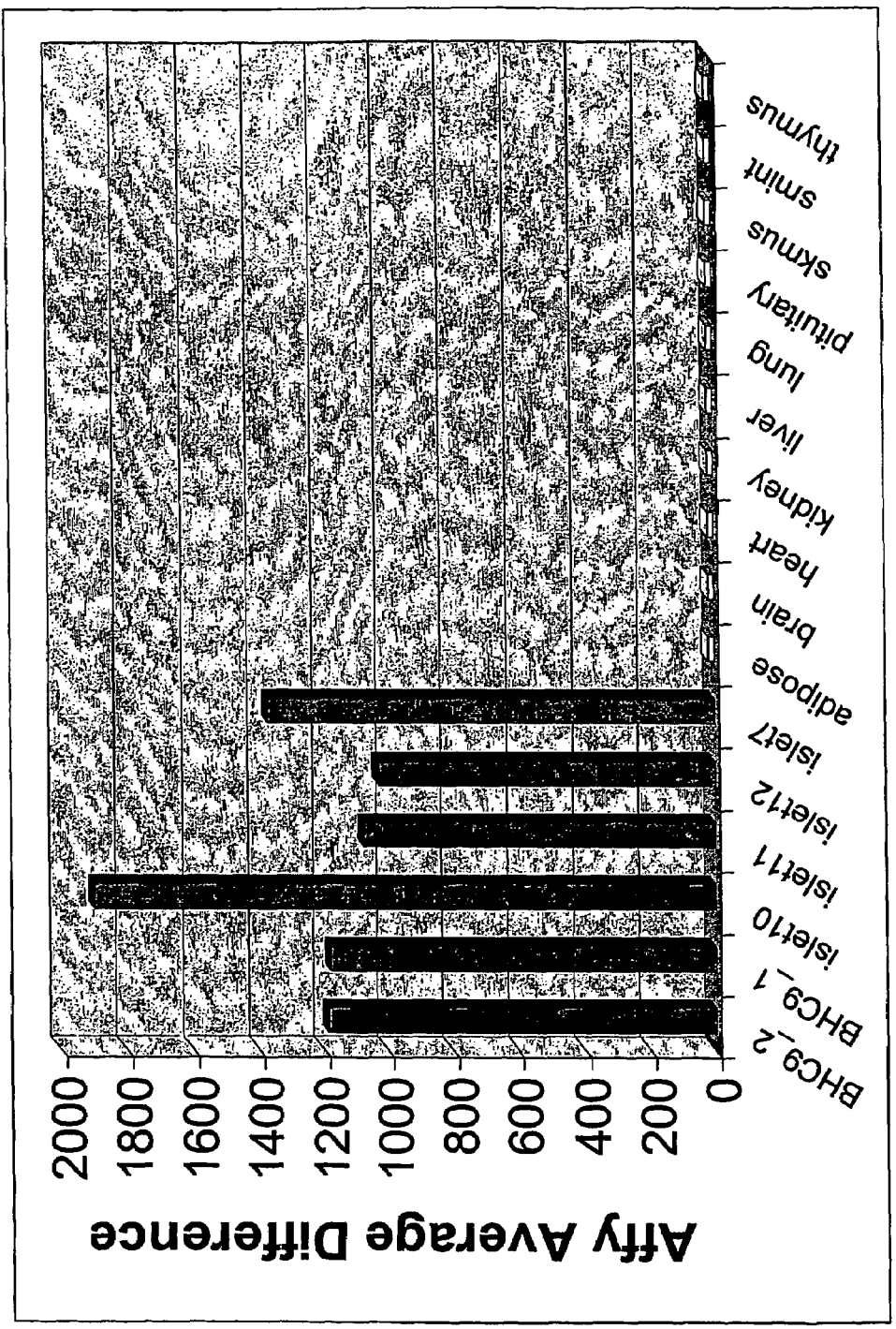
FIG. 3 illustrates that mouse IC-RFX is highly enriched in pancreatic islets. Average Difference values from a survey of identical quantities of mouse tissue RNAs or mouse beta cell lines were obtained by hybridization of samples to a custom mouse islet Affymetrix GeneChip array. Probe set MBXMU-SISL22609, which detects IC-RFX transcripts, displays strong hybridization signals with two samples of a mouse beta cell line (betaHC9_1, betaHC9_2) and four separate mouse islet RNA samples multiple different mice (islet7, islet10, islet11, islet12) but no hybridization signal to any of ten other mouse tissues (adipose, brain, heart, kidney, liver, lung, pituitary, skeletal muscle, small intestine, thymus).

Analysis of rat, mouse and human islet EST databases and expression profiling on custom islet Affymetrix oligonucleotide arrays revealed that ESTs and Affymetrix probe sets corresponding to IC-RFX are highly enriched in pancreatic islets and beta cells and are not detected in any other tissue examined (FIG. 1 and FIG. 3). These negative tissues include whole pancreas (islets compose less than 5% of total pancreas mRNA), adipose, brain, heart, kidney, liver, lung, skeletal muscle, small intestine or thymus, pituitary). Northern blots of human RNAs confirmed the specific expression of IC-RFX in islets (FIG. 2).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

SEQUENCE LISTING

```
<160> NUMBER OF SEQ ID NOS: 42

<210> SEQ ID NO 1
<211> LENGTH: 3048
<212> TYPE: DNA
<213> ORGANISM: Homo sapiens
<220> FEATURE:
<223> OTHER INFORMATION: human IC-RFX islet transcription factor cDNA

<400> SEQUENCE: 1
tttctgcgct gagccagggc accccggagc ctgcggcctc cttcccgcc cctgcggccc      60 cgggtcccag ccccgccccg ccccgccccg ggctggggct ccgctgggga accggccgag     120
cggcgcgcgc ggaggtgtcc ggcggccagg aggatggcca aggtcccgga gctggaagac     180
accttcctgc aggcgcagcc tgcgccccaa ctgtccccgg ggatccagga agactgctgt     240
gtgcagctcc tgggcaaggg cttgctagtc tatccggaag aaacagtgta cctggcggcc     300
```

-continued

| | |
|---|---|
| gaagggcagc ccgggggcga gcagggcggc ggggagaaag gcgaagaccc ggagctgccg | 360 |
| ggggcagtga atcagaaat gcacttaaac aatggtaact tttcctctga agaagaggac | 420 |
| gccgacaacc acgacagcaa aaccaaagca gcggatcaat acctgtctca gaagaaaacc | 480 |
| atcacgcaga ttgtgaagga taaaagaag cagacacagc tcacgctgca gtggcttgaa | 540 |
| gagaattaca ttgtatgtga aggagtttgc ttaccacggt gcattcttta tgcacactac | 600 |
| ttagatttct gtaggaaaga gaaattagag ccagcctgtg cggccacctt tggaaagaca | 660 |
| attcgccaga agtttcccct cctaacaaca aggcggcttg gaacaagagg ccattcaaag | 720 |
| tatcattact atgggattgg catcaaagag agcagtgcat attaccactc cgtttattct | 780 |
| ggaaagggct tgacaaggtt ttctggaagc aagctaaaga atgagggtgg cttcactcgt | 840 |
| aaatattcgc ttagctcaaa aactggaaca cttcttccag aattccccag cgctcaacac | 900 |
| cttgtatacc aaggatgcat ttctaaggac aaggttgata cgctcataat gatgtacaaa | 960 |
| actcactgcc agtgtatcct ggacaatgca attaatggaa actttgaaga atccagcat | 1020 |
| tttttattac acttttggca aggaatgcct gaccatctcc ttcccctgct cgaaaatcct | 1080 |
| gttatcattg atatttctg tgtttgtgac tcaattcttt ataaggttct tacagatgta | 1140 |
| ctcattcctg caacaatgca agaaatgcct gaaagcttat tagcagacat aagaaatttt | 1200 |
| gctaaaaatt gggaacagtg ggttgtttca tccttggaaa acttgccaga agctctaact | 1260 |
| gacaagaaaa tacctattgt gcgaagattt gtatcttctc tgaaacgaca acatctttc | 1320 |
| ttacatcttg cccagattgc cagaccagct ctctttgacc agcatgtcgt taattctatg | 1380 |
| gtgtctgata ttgaaagggt tgatttgaac agcattggct ctcaagccct tcttaccatt | 1440 |
| tcaggcagca cagacactga atctggtatc tacactgaac atgactctat cactgtgttc | 1500 |
| caagaactga aggatctcct taagaagaat gccactgtgg aggcttttat tgaatggttg | 1560 |
| gatactgtgg tagaacagag agttattaag accagcaaac aaaatggaag gtcattaaag | 1620 |
| aagagagctc aagactttct gttaaagtgg agttttttg gtgctcgagt aatgcataat | 1680 |
| ctcaccttga acaatgcatc cagttttggt tcttttcatt tgattcgaat gcttctcgat | 1740 |
| gaatacattc tcctggccat ggagacccag tttaataatg acaaagagca ggagttacag | 1800 |
| aatttattgg acaagtatat gaagaattca gatgcgagta agctgctttt cactgcttct | 1860 |
| ccgagttcat gctttctggc caaccgtaat aaagggagca tggtttccag cgacgctgtg | 1920 |
| aagaatgaaa gccacgtgga gacaacctat ctccctctgc catccagtca acctggaggc | 1980 |
| ctaggccctg ctctgcacca gttccctgct gggaacacag acaacatgcc gctcacaggt | 2040 |
| caaatggagc tttcacagat tgctggtcat ctgatgacac cacccatttc tccagccatg | 2100 |
| gcaagccgag gaagtgtcat taaccaagga ccaatggcag ggaggccccc aagtgtgggc | 2160 |
| ccagtactgt cagctccatc acactgctcc acatacccag agcccattta tcccactctc | 2220 |
| cctcaagcca atcatgactt ttatagcacc agctctaact accagactgt gtttagggca | 2280 |
| cagcccccact ccacatcagg actctatcct catcacaccg agcatggtcg atgcatggct | 2340 |
| tggactgaac agcagctttc aagagacttc ttcagtggca gctgtgcggg gtctccatat | 2400 |
| aactcccggc caccgtctag ctatggccca tccctgcaag cccaggattc acacaatatg | 2460 |
| cagttttaa atacaggaag cttcaatttc ttgagcaaca caggagctgc cagctgccaa | 2520 |
| ggagcaacac tgcctcctaa ttcaccaaat ggatactatg gaagcaacat aaactaccca | 2580 |
| gagtctcaca ggctcggatc aatggtgaat cagcacgttt ctgtcatcag cagcattcgt | 2640 |

-continued

```
tcactgcccc cctacagtga catccacgat ccacttaaca ttttagatga cagtggtaga    2700
aaacagacca gctcgtttta cacagacaca tcatctccag ttgcatgtcg aactccagtc    2760
ctagcttcca gtttgcaaac cccaattcct tcttcctcat cccaatgtat gtatggaact    2820
tccaaccagt atccagctca agaaaccctg gactcccatg aacaagcag tagagaaatg     2880 gtgtcctctt taccacctat caacactgtg ttcatgggaa cagcagctgg aggcacttaa    2940
accaccaatg tgggaggggg tgctaaaact ttaaaaaaaa tctctactgt gcaaatatca    3000
ttattcactc agacttccat aagagtaaat aaaaaatgaa tatgcagt                 3048
```

<210> SEQ ID NO 2
<211> LENGTH: 928
<212> TYPE: PRT
<213> ORGANISM: Homo sapiens
<220> FEATURE:
<223> OTHER INFORMATION: human IC-RFX islet transcription factor

<400> SEQUENCE: 2

```
Met Ala Lys Val Pro Glu Leu Glu Asp Thr Phe Leu Gln Ala Gln Pro
  1               5                  10                  15

Ala Pro Gln Leu Ser Pro Gly Ile Gln Glu Asp Cys Cys Val Gln Leu
             20                  25                  30

Leu Gly Lys Gly Leu Leu Val Tyr Pro Glu Glu Thr Val Tyr Leu Ala
         35                  40                  45

Ala Glu Gly Gln Pro Gly Gly Glu Gln Gly Gly Glu Lys Gly Glu
     50                  55                  60

Asp Pro Glu Leu Pro Gly Ala Val Lys Ser Glu Met His Leu Asn Asn
 65                  70                  75                  80

Gly Asn Phe Ser Ser Glu Glu Asp Ala Asp Asn His Asp Ser Lys
                 85                  90                  95

Thr Lys Ala Ala Asp Gln Tyr Leu Ser Gln Lys Lys Thr Ile Thr Gln
            100                 105                 110

Ile Val Lys Asp Lys Lys Gln Thr Gln Leu Thr Leu Gln Trp Leu
            115                 120                 125

Glu Glu Asn Tyr Ile Val Cys Glu Gly Val Cys Leu Pro Arg Cys Ile
    130                 135                 140

Leu Tyr Ala His Tyr Leu Asp Phe Cys Arg Lys Glu Lys Leu Glu Pro
145                 150                 155                 160

Ala Cys Ala Ala Thr Phe Gly Lys Thr Ile Arg Gln Lys Phe Pro Leu
                165                 170                 175

Leu Thr Thr Arg Arg Leu Gly Thr Arg Gly His Ser Lys Tyr His Tyr
            180                 185                 190

Tyr Gly Ile Gly Ile Lys Glu Ser Ser Ala Tyr Tyr His Ser Val Tyr
            195                 200                 205

Ser Gly Lys Gly Leu Thr Arg Phe Ser Gly Ser Lys Leu Lys Asn Glu
        210                 215                 220

Gly Gly Phe Thr Arg Lys Tyr Ser Leu Ser Ser Lys Thr Gly Thr Leu
225                 230                 235                 240

Leu Pro Glu Phe Pro Ser Ala Gln His Leu Val Tyr Gln Gly Cys Ile
                245                 250                 255

Ser Lys Asp Lys Val Asp Thr Leu Ile Met Met Tyr Lys Thr His Cys
            260                 265                 270

Gln Cys Ile Leu Asp Asn Ala Ile Asn Gly Asn Phe Glu Glu Ile Gln
        275                 280                 285

His Phe Leu Leu His Phe Trp Gln Gly Met Pro Asp His Leu Leu Pro
```

-continued

```
            290                 295                 300
Leu Leu Glu Asn Pro Val Ile Ile Asp Ile Phe Cys Val Cys Asp Ser
305                 310                 315                 320

Ile Leu Tyr Lys Val Leu Thr Asp Val Leu Ile Pro Ala Thr Met Gln
                325                 330                 335

Glu Met Pro Glu Ser Leu Leu Ala Asp Ile Arg Asn Phe Ala Lys Asn
                340                 345                 350

Trp Glu Gln Trp Val Val Ser Leu Glu Asn Leu Pro Glu Ala Leu
            355                 360                 365

Thr Asp Lys Lys Ile Pro Ile Val Arg Arg Phe Val Ser Ser Leu Lys
370                 375                 380

Arg Gln Thr Ser Phe Leu His Leu Ala Gln Ile Ala Arg Pro Ala Leu
385                 390                 395                 400

Phe Asp Gln His Val Val Asn Ser Met Val Ser Asp Ile Glu Arg Val
                405                 410                 415

Asp Leu Asn Ser Ile Gly Ser Gln Ala Leu Leu Thr Ile Ser Gly Ser
                420                 425                 430

Thr Asp Thr Glu Ser Gly Ile Tyr Thr Glu His Asp Ser Ile Thr Val
        435                 440                 445

Phe Gln Glu Leu Lys Asp Leu Leu Lys Lys Asn Ala Thr Val Glu Ala
    450                 455                 460

Phe Ile Glu Trp Leu Asp Thr Val Val Glu Gln Arg Val Ile Lys Thr
465                 470                 475                 480

Ser Lys Gln Asn Gly Arg Ser Leu Lys Lys Arg Ala Gln Asp Phe Leu
                485                 490                 495

Leu Lys Trp Ser Phe Phe Gly Ala Arg Val Met His Asn Leu Thr Leu
            500                 505                 510

Asn Asn Ala Ser Ser Phe Gly Ser Phe His Leu Ile Arg Met Leu Leu
        515                 520                 525

Asp Glu Tyr Ile Leu Leu Ala Met Glu Thr Gln Phe Asn Asn Asp Lys
    530                 535                 540

Glu Gln Glu Leu Gln Asn Leu Leu Asp Lys Tyr Met Lys Asn Ser Asp
545                 550                 555                 560

Ala Ser Lys Ala Ala Phe Thr Ala Ser Pro Ser Ser Cys Phe Leu Ala
                565                 570                 575

Asn Arg Asn Lys Gly Ser Met Val Ser Ser Asp Ala Val Lys Asn Glu
            580                 585                 590

Ser His Val Glu Thr Thr Tyr Leu Pro Leu Pro Ser Ser Gln Pro Gly
        595                 600                 605

Gly Leu Gly Pro Ala Leu His Gln Phe Pro Ala Gly Asn Thr Asp Asn
    610                 615                 620

Met Pro Leu Thr Gly Gln Met Glu Leu Ser Gln Ile Ala Gly His Leu
625                 630                 635                 640

Met Thr Pro Pro Ile Ser Pro Ala Met Ala Ser Arg Gly Ser Val Ile
                645                 650                 655

Asn Gln Gly Pro Met Ala Gly Arg Pro Pro Ser Val Gly Pro Val Leu
            660                 665                 670

Ser Ala Pro Ser His Cys Ser Thr Tyr Pro Glu Pro Ile Tyr Pro Thr
        675                 680                 685

Leu Pro Gln Ala Asn His Asp Phe Tyr Ser Thr Ser Ser Asn Tyr Gln
    690                 695                 700

Thr Val Phe Arg Ala Gln Pro His Ser Thr Ser Gly Leu Tyr Pro His
705                 710                 715                 720
```

```
His Thr Glu His Gly Arg Cys Met Ala Trp Thr Glu Gln Gln Leu Ser
                725                 730                 735

Arg Asp Phe Phe Ser Gly Ser Cys Ala Gly Ser Pro Tyr Asn Ser Arg
            740                 745                 750

Pro Pro Ser Ser Tyr Gly Pro Ser Leu Gln Ala Gln Asp Ser His Asn
        755                 760                 765

Met Gln Phe Leu Asn Thr Gly Ser Phe Asn Phe Leu Ser Asn Thr Gly
    770                 775                 780

Ala Ala Ser Cys Gln Gly Ala Thr Leu Pro Pro Asn Ser Pro Asn Gly
785                 790                 795                 800

Tyr Tyr Gly Ser Asn Ile Asn Tyr Pro Glu Ser His Arg Leu Gly Ser
                805                 810                 815

Met Val Asn Gln His Val Ser Val Ile Ser Ser Ile Arg Ser Leu Pro
            820                 825                 830

Pro Tyr Ser Asp Ile His Asp Pro Leu Asn Ile Leu Asp Asp Ser Gly
        835                 840                 845

Arg Lys Gln Thr Ser Ser Phe Tyr Thr Asp Thr Ser Ser Pro Val Ala
    850                 855                 860

Cys Arg Thr Pro Val Leu Ala Ser Ser Leu Gln Thr Pro Ile Pro Ser
865                 870                 875                 880

Ser Ser Ser Gln Cys Met Tyr Gly Thr Ser Asn Gln Tyr Pro Ala Gln
                885                 890                 895

Glu Thr Leu Asp Ser His Gly Thr Ser Ser Arg Glu Met Val Ser Ser
            900                 905                 910

Leu Pro Pro Ile Asn Thr Val Phe Met Gly Thr Ala Ala Gly Gly Thr
        915                 920                 925

<210> SEQ ID NO 3
<211> LENGTH: 928
<212> TYPE: PRT
<213> ORGANISM: Artificial Sequence
<220> FEATURE:
<223> OTHER INFORMATION: Description of Artificial Sequence:exemplary
      IC-RFX consensus sequence
<220> FEATURE:
<221> NAME/KEY: MOD_RES
<222> LOCATION: (1)..(928)
<223> OTHER INFORMATION: Xaa = any amino acid

<400> SEQUENCE: 3

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa Xaa
             35                  40                  45

Xaa Xaa Xaa Xaa Pro Gly Xaa Xaa Xaa Gly Gly Xaa Xaa Xaa Xaa Xaa
         50                  55                  60

Xaa Arg Xaa Xaa Xaa Xaa Xaa Xaa Xaa Glu Xaa Xaa Leu Asn Xaa Xaa
 65                  70                  75                  80

Gly Xaa Xaa Xaa Ser Glu Xaa Xaa Xaa Xaa Xaa Xaa His Xaa Ser Xaa
                 85                  90                  95

Xaa Xaa Xaa Xaa Xaa Xaa Xaa Xaa Xaa Lys Xaa Xaa Xaa Xaa Xaa Xaa
                100                 105                 110

Xaa Xaa Xaa Xaa Lys Xaa Xaa Xaa Thr Xaa Xaa Thr Leu Gln Trp Leu
            115                 120                 125
```

-continued

```
Glu Glu Asn Tyr Xaa Xaa Xaa Glu Gly Val Cys Leu Pro Arg Cys Xaa
            130                 135                 140

Leu Tyr Xaa His Tyr Leu Asp Phe Cys Xaa Lys Xaa Xaa Xaa Xaa Pro
145                 150                 155                 160

Xaa Xaa Ala Ala Xaa Phe Gly Lys Xaa Ile Arg Gln Xaa Phe Pro Xaa
                165                 170                 175

Leu Thr Thr Arg Arg Leu Gly Thr Arg Gly Xaa Ser Lys Tyr His Tyr
            180                 185                 190

Tyr Gly Ile Xaa Xaa Lys Glu Ser Ser Xaa Tyr Tyr Xaa Xaa Xaa Tyr
            195                 200                 205

Ser Xaa Lys Gly Xaa Xaa Xaa Ser Xaa Xaa Xaa Lys Xaa Xaa
        210                 215                 220

Xaa Xaa Xaa Thr Xaa Xaa Tyr Ser Xaa Xaa Ser Lys Xaa Gly Thr Leu
225                 230                 235                 240

Leu Pro Glu Phe Pro Xaa Xaa Gln His Xaa Xaa Xaa Xaa Xaa Xaa Ile
                245                 250                 255

Xaa Xaa Xaa Lys Val Xaa Thr Leu Ile Met Met Tyr Xaa Thr His Cys
            260                 265                 270

Gln Xaa Ile Leu Asp Xaa Xaa Ile Xaa Xaa Asn Phe Xaa Glu Xaa Gln
            275                 280                 285

Xaa Phe Leu Leu His Phe Trp Gln Gly Met Pro Asp His Xaa Leu Pro
    290                 295                 300

Leu Xaa Xaa Xaa Xaa Xaa Xaa Asp Ile Xaa Xaa Val Cys Asp Ser
305                 310                 315                 320

Ile Leu Tyr Lys Xaa Xaa Xaa Asp Val Leu Ile Pro Xaa Xaa Xaa Gln
            325                 330                 335

Glu Xaa Pro Xaa Ser Leu Xaa Xaa Xaa Ile Arg Xaa Phe Ala Lys Asn
        340                 345                 350

Xaa Xaa Xaa Trp Xaa Xaa Xaa Ser Leu Xaa Asn Leu Pro Glu Xaa Leu
            355                 360                 365

Xaa Xaa Lys Lys Ile Xaa Xaa Xaa Arg Arg Phe Xaa Xaa Xaa Leu Lys
            370                 375                 380

Arg Gln Thr Ser Xaa Xaa His Leu Ala Gln Xaa Xaa Arg Xaa Xaa Leu
385                 390                 395                 400

Xaa Xaa Xaa Xaa Xaa Val Xaa Xaa Met Xaa Xaa Asp Xaa Xaa Arg Val
                405                 410                 415

Asp Leu Asn Ser Ile Xaa Xaa Gln Ala Leu Xaa Thr Xaa Xaa Xaa Ser
            420                 425                 430

Xaa Asp Xaa Xaa Xaa Xaa Xaa Thr Xaa Xaa Xaa Xaa Xaa Xaa Xaa
    435                 440                 445

Xaa Gln Glu Xaa Lys Xaa Leu Leu Xaa Xaa Xaa Xaa Xaa Glu Xaa
    450                 455                 460

Xaa Ile Glu Trp Leu Asp Thr Xaa Val Xaa Gln Xaa Val Xaa Lys Xaa
465                 470                 475                 480

Xaa Xaa Xaa Xaa Xaa Xaa Ser Leu Lys Lys Xaa Ala Gln Xaa Phe Leu
                485                 490                 495

Leu Xaa Trp Ser Phe Phe Gly Xaa Arg Val Xaa Xaa Xaa Leu Thr Leu
        500                 505                 510

Xaa Xaa Ala Xaa Ser Phe Gly Ser Phe His Leu Ile Arg Xaa Leu Xaa
            515                 520                 525

Asp Xaa Tyr Xaa Leu Xaa Xaa Xaa Glu Xaa Xaa Xaa Xaa Xaa Xaa
        530                 535                 540

Xaa Gln Glu Xaa Xaa Asn Xaa Leu Xaa Xaa Xaa Met Lys Xaa Xaa Xaa
```

```
                  545                 550                 555                 560

Xaa Xaa Xaa Xaa Xaa Xaa Xaa Xaa Xaa Xaa Xaa Xaa Xaa Xaa Xaa
                  565                 570                 575

Xaa Xaa Xaa Xaa Gly Xaa Xaa Xaa Ser Xaa Xaa Xaa Val Xaa Xaa Glu
                  580                 585                 590

Xaa Xaa Xaa Xaa Xaa Xaa Xaa Xaa Pro Leu Pro Ser Xaa Xaa Xaa Xaa
              595                 600                 605

Xaa Xaa Xaa Xaa Xaa Xaa Xaa Xaa Xaa Xaa Xaa Xaa Xaa Xaa Xaa
              610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Pro Xaa Xaa Ser Pro Ala Xaa Xaa Xaa Xaa Xaa Xaa Xaa
              645                 650                 655

Xaa Xaa Xaa Xaa Xaa Xaa Xaa Xaa Pro Pro Xaa Xaa Xaa Xaa Xaa Xaa
              660                 665                 670

Xaa Xaa Xaa Xaa Xaa Xaa Xaa Xaa Xaa Xaa Xaa Xaa Xaa Xaa Xaa
              675                 680                 685

Xaa Xaa Xaa Xaa Xaa Xaa Xaa Xaa Ser Xaa Xaa Xaa Xaa Xaa Xaa
              690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
              725                 730                 735

Xaa Xaa Xaa Xaa Xaa Xaa Xaa Xaa Xaa Ser Pro Xaa Xaa Xaa Xaa
              740                 745                 750

Xaa Pro Ser Xaa Xaa Xaa Xaa Xaa Xaa Xaa Xaa Xaa Xaa Xaa Xaa
              755                 760                 765

Xaa Xaa Xaa Xaa Xaa Xaa Xaa Xaa Xaa Xaa Xaa Leu Ser Asn Thr Gly
              770                 775                 780

Xaa Xaa Xaa Xaa Xaa Xaa Xaa Xaa Xaa Xaa Xaa Xaa Xaa Xaa Asn Gly
785                 790                 795                 800

Xaa Xaa Xaa Xaa Asn Xaa Xaa Xaa Xaa Xaa Xaa Xaa Xaa Xaa Xaa
              805                 810                 815

Xaa Xaa Xaa Xaa Xaa Xaa Xaa Xaa Xaa Xaa Xaa Xaa Xaa Xaa Xaa
              820                 825                 830

Xaa Xaa Xaa Xaa Xaa Xaa Xaa Xaa Xaa Xaa Xaa Xaa Xaa Xaa Xaa
              835                 840                 845

Xaa Xaa Xaa Xaa Xaa Xaa Xaa Xaa Xaa Xaa Xaa Xaa Xaa Xaa Xaa
              850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa
              885                 890                 895

Xaa Xaa Xaa Xaa Xaa Xaa Xaa Xaa Xaa Xaa Xaa Xaa Xaa Xaa Xaa
              900                 905                 910

Xaa Xaa Xaa Xaa Xaa Xaa Xaa Xaa Xaa Xaa Xaa Xaa Xaa Xaa Xaa
              915                 920                 925

<210> SEQ ID NO 4
<211> LENGTH: 75
<212> TYPE: PRT
<213> ORGANISM: Artificial Sequence
<220> FEATURE:
<223> OTHER INFORMATION: Description of Artificial Sequence:RFX DNA
      binding domain (DBD) consensus sequence
```

-continued

```
<220> FEATURE:
<221> NAME/KEY: MOD_RES
<222> LOCATION: (1)..(75)
<223> OTHER INFORMATION: Xaa = any amino acid

<400> SEQUENCE: 4

Thr Leu Gln Trp Leu Xaa Xaa Asn Tyr Xaa Xaa Xaa Glu Gly Val Xaa
  1               5                  10                  15

Leu Pro Arg Xaa Xaa Leu Tyr Xaa His Tyr Leu Xaa Xaa Cys Xaa Xaa
             20                  25                  30

Xaa Lys Leu Glu Pro Xaa Xaa Ala Ala Xaa Phe Gly Lys Xaa Ile Arg
         35                  40                  45

Xaa Xaa Phe Xaa Xaa Leu Xaa Thr Arg Arg Leu Gly Thr Arg Gly Xaa
     50                  55                  60

Ser Lys Tyr His Tyr Tyr Gly Ile Xaa Xaa Lys
 65                  70                  75

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence:RFX B domain
      consensus sequence
<220> FEATURE:
<221> NAME/KEY: MOD_RES
<222> LOCATION: (1)..(35)
<223> OTHER INFORMATION: Xaa = any amino acid

<400> SEQUENCE: 5

Val Xaa Xaa Leu Xaa Xaa Xaa Tyr Xaa Xaa His Cys Xaa Xaa Ile Leu
  1               5                  10                  15

Asp Xaa Xaa Xaa Asn Xaa Xaa Phe Xaa Xaa Xaa Xaa Xaa Xaa Xaa Xaa
             20                  25                  30

Xaa Phe Trp
         35

<210> SEQ ID NO 6
<211> LENGTH: 40
<212> TYPE: PRT
<213> ORGANISM: Artificial Sequence
<220> FEATURE:
<223> OTHER INFORMATION: Description of Artificial Sequence:RFX C domain
      consensus sequence
<220> FEATURE:
<221> NAME/KEY: MOD_RES
<222> LOCATION: (1)..(40)
<223> OTHER INFORMATION: Xaa = any amino acid

<400> SEQUENCE: 6

Leu Tyr Xaa Xaa Xaa Xaa Xaa Xaa Leu Ile Pro Xaa Xaa Xaa Xaa Xaa
  1               5                  10                  15

Xaa Pro Xaa Xaa Leu Xaa Xaa Xaa Ile Arg Xaa Phe Ala Lys Xaa Xaa
             20                  25                  30

Xaa Xaa Trp Xaa Xaa Xaa Xaa Leu
         35                  40

<210> SEQ ID NO 7
<211> LENGTH: 170
<212> TYPE: PRT
<213> ORGANISM: Artificial Sequence
<220> FEATURE:
<223> OTHER INFORMATION: Description of Artificial Sequence:RFX
      dimerization domain consensus sequence
<220> FEATURE:

```
<221> NAME/KEY: MOD_RES
<222> LOCATION: (1)..(170)
<223> OTHER INFORMATION: Xaa = any amino acid

<400> SEQUENCE: 7

Phe Xaa Xaa Xaa Leu Xaa Arg Xaa Thr Ser Xaa Xaa His Leu Ala Gln
 1               5                  10                  15

Xaa Ala Arg Xaa Xaa Leu Xaa Xaa Xaa Xaa Xaa Asn Xaa Met Xaa
            20                  25                  30

Ser Asp Xaa Xaa Arg Val Asp Xaa Asn Xaa Xaa Xaa Xaa Gln Ala Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Gln Xaa Xaa Lys Xaa Xaa Leu Xaa Xaa
 65                 70                  75                  80

Xaa Xaa Xaa Xaa Glu Xaa Xaa Xaa Glu Trp Leu Asp Xaa Val Xaa Xaa
                85                  90                  95

Gln Xaa Xaa Xaa Xaa Xaa Xaa Tyr Xaa Xaa Xaa Xaa Xaa Xaa Xaa Lys
            100                 105                 110

Xaa Ala Xaa Xaa Phe Leu Leu Lys Trp Ser Phe Xaa Xaa Xaa Xaa Val
        115                 120                 125

Xaa Xaa Xaa Leu Thr Leu Xaa Xaa Ala Xaa Ser Phe Gly Ser Phe His
130                 135                 140

Leu Ile Arg Xaa Leu Xaa Asp Glu Tyr Xaa Xaa Xaa Xaa Xaa Glu Xaa
145                 150                 155                 160

Xaa Xaa Xaa Xaa Xaa Xaa Xaa Xaa Xaa Leu
            165                 170

<210> SEQ ID NO 8
<211> LENGTH: 76
<212> TYPE: PRT
<213> ORGANISM: Artificial Sequence
<220> FEATURE:
<223> OTHER INFORMATION: Description of Artificial Sequence:exemplary
      RFX DNA binding domain (DBD)

<400> SEQUENCE: 8

Thr Leu Gln Trp Leu Glu Glu Asn Tyr Ile Val Cys Glu Gly Val Cys
 1               5                  10                  15

Leu Pro Arg Cys Ile Leu Tyr Ala His Tyr Leu Asp Phe Cys Arg Lys
            20                  25                  30

Glu Lys Leu Glu Pro Ala Cys Ala Ala Thr Phe Gly Lys Thr Ile Arg
        35                  40                  45

Gln Lys Phe Pro Leu Leu Thr Thr Arg Arg Leu Gly Thr Arg Gly His
    50                  55                  60

Ser Lys Tyr His Tyr Tyr Gly Ile Gly Ile Lys Glu
 65                 70                  75

<210> SEQ ID NO 9
<211> LENGTH: 36
<212> TYPE: PRT
<213> ORGANISM: Artificial Sequence
<220> FEATURE:
<223> OTHER INFORMATION: Description of Artificial Sequence:exemplary
      RFX B domain

<400> SEQUENCE: 9

Lys Val Asp Thr Leu Ile Met Met Tyr Lys Thr His Cys Gln Cys Ile
 1               5                  10                  15
```

-continued

```
Leu Asp Asn Ala Ile Asn Gly Asn Phe Glu Glu Ile Gln His Phe Leu
            20                  25                  30

Leu His Phe Trp
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence:exemplary
      RFX C domain

<400> SEQUENCE: 10

Leu Tyr Lys Val Leu Thr Asp Val Leu Ile Pro Ala Thr Met Gln Glu
  1               5                  10                  15

Met Pro Glu Ser Leu Leu Ala Asp Ile Arg Asn Phe Ala Lys Asn Trp
            20                  25                  30

Glu Gln Trp Val Val Ser Ser Leu
        35                  40

<210> SEQ ID NO 11
<211> LENGTH: 179
<212> TYPE: PRT
<213> ORGANISM: Artificial Sequence
<220> FEATURE:
<223> OTHER INFORMATION: Description of Artificial Sequence:exemplary
      RFX dimerization domain

<400> SEQUENCE: 11

Arg Phe Val Ser Ser Leu Lys Arg Gln Thr Ser Phe Leu His Leu Ala
  1               5                  10                  15

Gln Ile Ala Arg Pro Ala Leu Phe Asp Gln His Val Val Asn Ser Met
            20                  25                  30

Val Ser Asp Ile Glu Arg Val Asp Leu Asn Ser Ile Gly Ser Gln Ala
        35                  40                  45

Leu Leu Thr Ile Ser Gly Ser Thr Asp Thr Glu Ser Gly Ile Tyr Thr
     50                  55                  60

Glu His Asp Ser Ile Thr Val Phe Gln Glu Leu Lys Asp Leu Leu Lys
 65                  70                  75                  80

Lys Asn Ala Thr Val Glu Ala Phe Ile Glu Trp Leu Asp Thr Val Val
                85                  90                  95

Glu Gln Arg Val Ile Lys Thr Ser Lys Gln Asn Gly Arg Ser Leu Lys
            100                 105                 110

Lys Arg Ala Gln Asp Phe Leu Leu Lys Trp Ser Phe Phe Gly Ala Arg
        115                 120                 125

Val Met His Asn Leu Thr Leu Asn Asn Ala Ser Ser Phe Gly Ser Phe
    130                 135                 140

His Leu Ile Arg Met Leu Leu Asp Glu Tyr Ile Leu Leu Ala Met Glu
145                 150                 155                 160

Thr Gln Phe Asn Asn Asp Lys Glu Gln Glu Leu Gln Asn Leu Leu Asp
                165                 170                 175

Lys Tyr Met

<210> SEQ ID NO 12
<211> LENGTH: 76
<212> TYPE: PRT
<213> ORGANISM: Artificial Sequence
<220> FEATURE:
<223> OTHER INFORMATION: Description of Artificial Sequence:RFX4 DNA
``` binding domain

<400> SEQUENCE: 12

Thr Leu Gln Trp Leu Glu Glu Asn Tyr Glu Ile Ala Glu Gly Val Cys
1               5                   10                  15

Ile Pro Arg Ser Ala Leu Tyr Met His Tyr Leu Asp Phe Cys Glu Lys
            20                  25                  30

Asn Asp Thr Gln Pro Val Asn Ala Ala Ser Phe Gly Lys Ile Ile Arg
        35                  40                  45

Gln Gln Phe Pro Gln Leu Thr Thr Arg Arg Leu Gly Thr Arg Gly Gln
    50                  55                  60

Ser Lys Tyr His Tyr Tyr Gly Ile Ala Val Lys Glu
65                  70                  75

<210> SEQ ID NO 13
<211> LENGTH: 77
<212> TYPE: PRT
<213> ORGANISM: Artificial Sequence
<220> FEATURE:
<223> OTHER INFORMATION: Description of Artificial Sequence:RFX5 DNA
      binding domain

<400> SEQUENCE: 13

Ala Tyr Arg Trp Ile Arg Asn His Leu Glu Glu His Thr Asp Thr Cys
1               5                   10                  15

Leu Pro Lys Gln Ser Val Tyr Asp Ala Tyr Arg Lys Tyr Cys Glu Ser
            20                  25                  30

Leu Ala Cys Cys Arg Pro Leu Ser Thr Ala Asn Phe Gly Lys Ile Ile
        35                  40                  45

Arg Glu Ile Phe Pro Asp Ile Lys Ala Arg Arg Leu Gly Gly Arg Gly
    50                  55                  60

Gln Ser Lys Tyr Cys Tyr Ser Gly Ile Arg Arg Lys Thr
65                  70                  75

<210> SEQ ID NO 14
<211> LENGTH: 75
<212> TYPE: PRT
<213> ORGANISM: Artificial Sequence
<220> FEATURE:
<223> OTHER INFORMATION: Description of Artificial Sequence:C. elegans
      RFX protein daf-19 DNA binding domain

<400> SEQUENCE: 14

Thr Val Asn Trp Leu Phe Glu Asn Tyr Glu Ile Gly Glu Gly Ser Leu
1               5                   10                  15

Pro Arg Cys Glu Leu Tyr Asp His Tyr Lys Lys His Cys Ala Glu His
            20                  25                  30

Arg Met Asp Pro Val Asn Ala Ala Ser Phe Gly Lys Leu Ile Arg Ser
        35                  40                  45

Val Phe His Asn Leu Lys Thr Arg Arg Leu Gly Thr Arg Gly Asn Ser
    50                  55                  60

Lys Tyr His Tyr Tyr Gly Ile Arg Leu Lys Asp
65                  70                  75

<210> SEQ ID NO 15
<211> LENGTH: 76
<212> TYPE: PRT
<213> ORGANISM: Artificial Sequence
<220> FEATURE:
<223> OTHER INFORMATION: Description of Artificial Sequence:RFX3 DNA
      binding domain

```
<400> SEQUENCE: 15

His Leu Gln Trp Leu Leu Asp Asn Tyr Glu Thr Ala Glu Gly Val Ser
1               5                   10                  15

Leu Pro Arg Ser Thr Leu Tyr Asn His Tyr Leu Arg His Cys Gln Glu
            20                  25                  30

His Lys Leu Asp Pro Val Asn Ala Ala Ser Phe Gly Lys Leu Ile Arg
        35                  40                  45

Ser Ile Phe Met Gly Leu Arg Thr Arg Leu Gly Thr Arg Gly Asn
    50                  55                  60

Ser Lys Tyr His Tyr Tyr Gly Ile Arg Val Lys Pro
65                  70                  75

<210> SEQ ID NO 16
<211> LENGTH: 76
<212> TYPE: PRT
<213> ORGANISM: Artificial Sequence
<220> FEATURE:
<223> OTHER INFORMATION: Description of Artificial Sequence:RFX2 DNA
      binding domain

<400> SEQUENCE: 16

His Leu Gln Trp Leu Leu Asp Asn Tyr Glu Thr Ala Glu Gly Val Ser
1               5                   10                  15

Leu Pro Arg Ser Ser Leu Tyr Asn His Tyr Leu Arg His Cys Gln Glu
            20                  25                  30

His Lys Leu Asp Pro Val Asn Ala Ala Ser Phe Gly Lys Leu Ile Arg
        35                  40                  45

Ser Val Phe Met Gly Leu Arg Thr Arg Leu Gly Thr Arg Gly Asn
    50                  55                  60

Ser Lys Tyr His Tyr Tyr Gly Ile Arg Leu Lys Pro
65                  70                  75

<210> SEQ ID NO 17
<211> LENGTH: 76
<212> TYPE: PRT
<213> ORGANISM: Artificial Sequence
<220> FEATURE:
<223> OTHER INFORMATION: Description of Artificial Sequence:RFX1 DNA
      binding domain

<400> SEQUENCE: 17

Thr Val Gln Trp Leu Leu Asp Asn Tyr Glu Thr Ala Glu Gly Val Ser
1               5                   10                  15

Leu Pro Arg Ser Thr Leu Tyr Cys His Tyr Leu Leu His Cys Gln Glu
            20                  25                  30

Gln Lys Leu Glu Pro Val Asn Ala Ala Ser Phe Gly Lys Leu Ile Arg
        35                  40                  45

Ser Val Phe Met Gly Leu Arg Thr Arg Leu Gly Thr Arg Gly Asn
    50                  55                  60

Ser Lys Tyr His Tyr Tyr Gly Leu Arg Ile Lys Ala
65                  70                  75

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:RFX DNA
      binding domain consensus sequence
```

-continued

```
<400> SEQUENCE: 18

Thr Leu Gln Trp Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:RFX DNA
      binding domain consensus sequence

<400> SEQUENCE: 19

Ala Glu Gly Val Ser Leu Pro Arg Ser
1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:RFX DNA
      binding domain consensus sequence

<400> SEQUENCE: 20

Pro Val Asn Ala Ala Ser Phe Gly Lys Leu Ile Arg Ser
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:RFX DNA
      binding domain consensus sequence

<400> SEQUENCE: 21

Thr Arg Arg Leu Gly Thr Arg Gly Asn Ser Lys Tyr His Tyr Tyr Gly
1               5                   10                  15

Ile Arg

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence:C. elegans
      RFX protein daf-19 B domain

<400> SEQUENCE: 22

Glu Leu Asn Ser Leu Ile Asp Ile Tyr Glu Ile Leu Cys Arg Glu Ile
1               5                   10                  15

Leu Ala Leu Ile Lys Asn Ile Asp Phe Ala Ser Val Glu Asp Thr Trp
            20                  25                  30

Ser Lys Phe Trp
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence:RFX1 B
      domain

<400> SEQUENCE: 23
```

```
Asp Ile Lys Ala Phe Gln Val Leu Tyr Arg Glu His Cys Glu Ala Ile
 1               5                  10                  15

Val Asp Val Met Val Asn Leu Gln Phe Thr Leu Val Glu Thr Leu Trp
            20                  25                  30

Lys Thr Phe Trp
         35

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence:RFX2 B
      domain

<400> SEQUENCE: 24

Asp Val Lys Ala Leu Gln Leu Val Tyr Arg Arg His Cys Glu Ala Thr
 1               5                  10                  15

Val Asp Val Val Met Asn Leu Gln Phe His Tyr Ile Glu Lys Leu Trp
            20                  25                  30

Leu Ser Phe Trp
         35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence:RFX4 B
      domain

<400> SEQUENCE: 25

Lys Val Ser Thr Phe Ile Met Met Tyr Arg Thr His Cys Gln Arg Ile
 1               5                  10                  15

Leu Asp Thr Val Ile Arg Ala Asn Phe Asp Glu Val Gln Ser Phe Leu
            20                  25                  30

Leu His Phe Trp
         35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence:RFX3 B
      domain

<400> SEQUENCE: 26

Asp Ile Lys Ser Leu Gln Ser Leu Tyr Arg Glu His Cys Glu Ala Ile
 1               5                  10                  15

Leu Asp Val Val Val Asn Leu Gln Phe Ser Leu Ile Glu Lys Leu Trp
            20                  25                  30

Gln Thr Phe Trp
         35

<210> SEQ ID NO 27
<211> LENGTH: 40
<212> TYPE: PRT
<213> ORGANISM: Artificial Sequence
<220> FEATURE:
<223> OTHER INFORMATION: Description of Artificial Sequence:RFX4 C
      domain
```

-continued

```
<400> SEQUENCE: 27

Leu Tyr Lys Ala Ile Ser Gly Val Leu Met Pro Thr Val Leu Gln Ala
 1               5                  10                  15

Leu Pro Asp Ser Leu Thr Gln Val Ile Arg Lys Phe Ala Lys Gln Leu
             20                  25                  30

Asp Glu Trp Leu Lys Val Ala Leu
         35                  40

<210> SEQ ID NO 28
<211> LENGTH: 40
<212> TYPE: PRT
<213> ORGANISM: Artificial Sequence
<220> FEATURE:
<223> OTHER INFORMATION: Description of Artificial Sequence:RFX1 C
      domain

<400> SEQUENCE: 28

Leu Tyr Gln Gly Leu Val Glu Ile Leu Ile Pro Asp Val Leu Arg Pro
 1               5                  10                  15

Ile Pro Ser Ala Leu Thr Gln Ala Ile Arg Asn Phe Ala Lys Ser Leu
             20                  25                  30

Glu Ser Trp Leu Thr His Ala Met
         35                  40

<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence:C. elegans
      RFX protein daf-19 C domain

<400> SEQUENCE: 29

Leu Tyr Gln Thr Ile Val Asp Thr Leu Ile Pro Asn Val Leu Leu Ser
 1               5                  10                  15

Glu Leu Ser Thr Gly Met Thr Gln Thr Cys Arg Thr Phe Ala Lys Asn
             20                  25                  30

Ile Asp Val Tyr Leu Arg Lys Ser Leu
         35                  40

<210> SEQ ID NO 30
<211> LENGTH: 174
<212> TYPE: PRT
<213> ORGANISM: Artificial Sequence
<220> FEATURE:
<223> OTHER INFORMATION: Description of Artificial Sequence:RFX4
      dimerization domain

<400> SEQUENCE: 30

Arg Phe Ser Gln Ile Leu Arg Arg Gln Thr Ser Leu Asn His Leu Cys
 1               5                  10                  15

Gln Ala Ser Arg Thr Val Ile His Ser Ala Asp Ile Thr Phe Gln Met
             20                  25                  30

Leu Glu Asp Trp Arg Asn Val Asp Leu Asn Ser Ile Thr Lys Gln Thr
         35                  40                  45

Leu Tyr Thr Met Glu Asp Ser Arg Asp Glu His Arg Lys Leu Ile Thr
     50                  55                  60

Gln Leu Tyr Gln Glu Phe Asp His Leu Leu Glu Glu Gln Ser Pro Ile
 65                  70                  75                  80

Glu Ser Tyr Ile Glu Trp Leu Asp Thr Met Val Asp Arg Cys Val Val
                 85                  90                  95
```

```
Lys Val Ala Ala Lys Arg Gln Gly Ser Leu Lys Lys Val Ala Gln Gln
            100                 105                 110

Phe Leu Leu Met Trp Ser Cys Phe Gly Thr Arg Val Ile Arg Asp Met
            115                 120                 125

Thr Leu His Ser Ala Pro Ser Phe Gly Ser Phe His Leu Ile His Leu
            130                 135                 140

Met Phe Asp Asp Tyr Val Leu Tyr Leu Glu Ser Leu His Cys Gln
145                 150                 155                 160

Glu Arg Ala Asn Glu Leu Met Arg Ala Met Lys Gly Glu Gly
                165                 170

<210> SEQ ID NO 31
<211> LENGTH: 170
<212> TYPE: PRT
<213> ORGANISM: Artificial Sequence
<220> FEATURE:
<223> OTHER INFORMATION: Description of Artificial Sequence:C. elegans
      RFX protein daf-19 dimerization domain

<400> SEQUENCE: 31

Tyr Leu Gln Gln Gly Leu Lys Arg Tyr Thr Ser Leu Asn His Leu Ala
 1               5                  10                  15

His Ala Ser Arg Gly Val Leu Met Lys Pro Glu Gln Val Gln Gln Met
             20                  25                  30

Tyr Gln Asp Tyr Ile Arg Val Asp Ile Asn Thr Val His Gln Gln Ala
         35                  40                  45

Gly Trp Ile Cys Gly Cys Asp Ser Val Met Val His His Val Asn Asn
     50                  55                  60

Ala Phe Lys His Asn Leu Gln Arg Met Ser Ala Met Glu Val Trp Ala
 65                  70                  75                  80

Glu Trp Leu Glu Ser Ile Val Asp Gln Val Leu Ala Lys Tyr His Asp
                 85                  90                  95

Lys Pro Ala Asn Val Ile Ala Asn Val Gly Lys Gln Phe Leu Leu Asn
            100                 105                 110

Trp Ser Phe Tyr Thr Ser Met Ile Ile Arg Asp Leu Thr Leu Arg Ser
            115                 120                 125

Ala Met Ser Phe Gly Ser Phe Thr Leu Ile Arg Leu Leu Ala Asp Asp
            130                 135                 140

Tyr Met Tyr Tyr Leu Ile Glu Ser Lys Ile Ala Lys Ala Gly Lys Gln
145                 150                 155                 160

Gln Leu Ile Thr Val Ile Arg Ala Asp Lys
                165                 170

<210> SEQ ID NO 32
<211> LENGTH: 168
<212> TYPE: PRT
<213> ORGANISM: Artificial Sequence
<220> FEATURE:
<223> OTHER INFORMATION: Description of Artificial Sequence:RFX3
      dimerization domain

<400> SEQUENCE: 32

Ala Phe Ala Gln Thr Leu Arg Arg Tyr Thr Ser Leu Asn His Leu Ala
 1               5                  10                  15

Gln Ala Ala Arg Ala Val Leu Gln Asn Thr Ser Gln Ile Asn Gln Met
             20                  25                  30

Leu Ser Asp Leu Asn Arg Val Asp Phe Ala Asn Val Gln Glu Gln Ala
         35                  40                  45
```

```
Ser Trp Val Cys Gln Cys Asp Asp Asn Met Val Gln Arg Leu Glu Thr
     50                  55                  60

Asp Phe Lys Met Thr Leu Gln Gln Gln Ser Thr Leu Glu Gln Trp Ala
 65                  70                  75                  80

Ala Trp Leu Asp Asn Val Met Met Gln Ala Leu Lys Pro Tyr Glu Gly
                 85                  90                  95

Arg Pro Ser Phe Pro Lys Ala Ala Arg Gln Phe Leu Leu Lys Trp Ser
            100                 105                 110

Phe Tyr Ser Ser Met Val Ile Arg Asp Leu Thr Leu Arg Ser Ala Ala
            115                 120                 125

Ser Phe Gly Ser Phe His Leu Ile Arg Leu Leu Tyr Asp Glu Tyr Met
    130                 135                 140

Phe Tyr Leu Val Glu His Arg Val Ala Gln Ala Thr Gly Glu Thr Pro
145                 150                 155                 160

Ile Ala Val Met Gly Glu Val Arg
                165
```

<210> SEQ ID NO 33
<211> LENGTH: 168
<212> TYPE: PRT
<213> ORGANISM: Artificial Sequence
<220> FEATURE:
<223> OTHER INFORMATION: Description of Artificial Sequence:RFX1
      dimerization domain

<400> SEQUENCE: 33

```
Ala Phe Ala Gln Thr Leu Arg Arg Tyr Thr Ser Leu Asn His Leu Ala
 1               5                  10                  15

Gln Ala Ala Arg Ala Val Leu Gln Asn Thr Ala Gln Ile Asn Gln Met
                 20                  25                  30

Leu Ser Asp Leu Asn Arg Val Asp Phe Ala Asn Val Gln Glu Gln Ala
             35                  40                  45

Ser Trp Val Cys Arg Cys Glu Asp Arg Val Val Gln Arg Leu Glu Gln
     50                  55                  60

Asp Phe Lys Val Thr Leu Gln Gln Gln Asn Ser Leu Glu Gln Trp Ala
 65                  70                  75                  80

Ala Trp Leu Asp Gly Val Val Ser Gln Val Leu Lys Pro Tyr Gln Gly
                 85                  90                  95

Ser Ala Gly Phe Pro Lys Ala Ala Lys Leu Phe Leu Leu Lys Trp Ser
            100                 105                 110

Phe Tyr Ser Ser Met Val Ile Arg Asp Leu Thr Leu Arg Ser Ala Ala
            115                 120                 125

Ser Phe Gly Ser Phe His Leu Ile Arg Leu Leu Tyr Asp Glu Tyr Met
    130                 135                 140

Tyr Tyr Leu Ile Glu His Arg Val Ala Gln Ala Lys Gly Glu Thr Pro
145                 150                 155                 160

Ile Ala Val Met Gly Glu Phe Ala
                165
```

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:RFX
      dimerization domain consensus sequence

<400> SEQUENCE: 34

Leu Arg Arg Tyr Thr Ser Leu Asn His Leu Ala Gln Ala Ala Arg
  1               5                  10                  15

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:RFX
      dimerization domain consensus sequence

<400> SEQUENCE: 35

Asn Gln Met Leu Ser Asp
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:RFX
      dimerization domain consensus sequence

<400> SEQUENCE: 36

Trp Ala Glu Trp Leu Asp
  1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:RFX
      dimerization domain consensus sequence

<400> SEQUENCE: 37

Gln Phe Leu Leu Lys Trp Ser Phe Tyr
  1               5

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence:RFX
      dimerization domain consensus sequence

<400> SEQUENCE: 38

Ser Met Val Ile Arg Asp Leu Thr Leu Arg Ser Ala
  1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence:RFX
      dimerization domain consensus sequence

<400> SEQUENCE: 39

Ser Phe Gly Ser Phe His Leu Ile Arg Leu Leu
  1               5                  10

<210> SEQ ID NO 40
<211> LENGTH: 4
<212> TYPE: PRT
<213> ORGANISM: Artificial Sequence

```
<220> FEATURE:
<223> OTHER INFORMATION: Description of Artificial Sequence:RFX
      dimerization domain consensus sequence

<400> SEQUENCE: 40

Asp Glu Tyr Met
 1

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence:
      hexahistidine (His) affinity tag

<400> SEQUENCE: 41

His His His His His His
 1               5

<210> SEQ ID NO 42
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 42

Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
 65                 70                  75                  80

Gly Gly Gly Gly Gly Gly Gly Gly Gly Gly Gly Gly Gly Gly Gly
            85                  90                  95

Gly Gly Gly Gly Gly Gly Gly Gly Gly Gly Gly Gly Gly Gly Gly
        100                 105                 110

Gly Gly Gly Gly Gly Gly Gly Gly Gly Gly Gly Gly Gly Gly Gly
    115                 120                 125

Gly Gly Gly Gly Gly Gly Gly Gly Gly Gly Gly Gly Gly Gly Gly
130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly
        180                 185                 190

Gly Gly Gly Gly Gly Gly Gly Gly
    195                 200
```

What is claimed is:

1. An isolated nucleic acid encoding an IC-RFX polypeptide comprising SEQ ID NO:2.

2. The nucleic acid of claim 1, wherein the nucleic acid comprises SEQ ID NO:1.

3. An isolated nucleic acid encoding a polypeptide comprising in the following order: a proline/glutamine rich domain, an RFX DNA binding domain (SEQ ID NO:4), an RFX B domain (SEQ ID NO:5), an RFX C domain (SEQ ID NO:6), a dimerization domain (SEQ ID NO:7) and a serine/threonine domain.

4. An expression cassette comprising a promoter operably linked to the nucleic acid of claim 1 or claim 3.

5. An isolated host cell transfected with the nucleic acid of claim 1 or claim 3.

6. The host cell of claim 5, wherein the cell is a pancreatic islet cell.

7. The host cell of claim 6, wherein the cell is an islet β-cell.

8. A method of detecting a polynucleotide in a subject, the method comprising detecting in a sample from the subject a polynucleotide encoding a polypeptide comprising in the following order: a proline/glutamine rich domain, an RFX DNA binding domain (SEQ ID NO:4), an RFX B domain (SEQ ID NO:5), an RFX C domain (SEQ ID NO:6), a dimerization domain (SEQ ID NO:7) and a serine/threonine domain.

9. The method of claim 8, wherein the polynucleotide is detected by hybridization.

10. The method of claim 8, wherein the polynucleotide is detected by amplification of the polynucleotide.

11. The method of claim 8, wherein the nucleotide sequence of the polynucleotide is determined.

12. A method of introducing an expression cassette into an isolated cell, the method comprising, introducing into the cell an expression cassette comprising a promoter operably linked to a polynucleotide encoding a polypeptide, the polypeptide comprising in the following order: a proline/glutamine rich domain, an RFX DNA binding domain (SEQ ID NO:4), an RFX B domain (SEQ ID NO:5), an FRX C domain (SEQ ID NO:6), a dimerization domain (SEQ ID NO:7) and a serine/threonine domain.

13. The method of claim 12, wherein the polypeptide comprises SEQ ID NO:2.

14. The method of claim 12, wherein the polynucleotide comprises SEQ ID NO:1.

15. The method of claim 12, wherein the cell is a pancreatic islet cell.

16. The method of claim 12, wherein the cell is an islet β-cell.

* * * * *